15 (12) United States Patent
Pisarnwongs et al.

(10) Patent No.: US 11,395,649 B2
(45) Date of Patent: *Jul. 26, 2022

(54) SUTURE PASSING DEVICE

(71) Applicant: ARCH DAY DESIGN, LLC, Ventura, CA (US)

(72) Inventors: Roger Pisarnwongs, Santa Clarita, CA (US); Thomas Weisel, Ventura, CA (US); Kevin Glen, Ventura, CA (US)

(73) Assignee: ARCH DAY DESIGN, LLC, Ventura, CA (US)

( * ) Notice: Subject to any disclaimer, the term of this patent is extended or adjusted under 35 U.S.C. 154(b) by 68 days.

This patent is subject to a terminal disclaimer.

(21) Appl. No.: 16/844,570

(22) Filed: Apr. 9, 2020

(65) Prior Publication Data

US 2020/0229810 A1 Jul. 23, 2020

Related U.S. Application Data

(63) Continuation of application No. 16/400,681, filed on May 1, 2019, now Pat. No. 10,646,217.

(60) Provisional application No. 62/689,388, filed on Jun. 25, 2018, provisional application No. 62/667,021, filed on May 4, 2018.

(51) Int. Cl.
*A61B 17/04* (2006.01)
(52) U.S. Cl.
CPC ...... *A61B 17/0482* (2013.01); *A61B 17/0483* (2013.01); *A61B 17/0469* (2013.01)
(58) Field of Classification Search
CPC ............ A61B 17/0482; A61B 17/0483; A61B 17/0169; A61B 17/3207; A61B 17/0485; A61B 17/06061; A61B 17/29; A61B 17/2909; A61B 17/30; A61B 17/28; A61B 17/282; A61B 17/2017; A61B 17/2937;
(Continued)

(56) References Cited

U.S. PATENT DOCUMENTS 3,879,813 A 4/1975 Shadwell
5,059,201 A 10/1991 Asnis
(Continued)

FOREIGN PATENT DOCUMENTS

DE 102012100083 A1 9/2012
WO 2012093094 A1 7/2012

OTHER PUBLICATIONS

International Preliminary Report on Patentability (Chapter II) dated Feb. 2, 2021 from PCT Application No. PCT/US2020/070307.
(Continued)

*Primary Examiner* — Katherine M Shi
*Assistant Examiner* — Paige A Codrington
(74) *Attorney, Agent, or Firm* — Innovation Capital Law Group, LLP; Vic Lin

(57) ABSTRACT

A suture passing device includes a jaw assembly that is moved to an open configuration after exiting a hollow needle distal tip and moved to a closed configuration when retracted into the needle tip. The jaw assembly may include a pair of jaw members biased to a default diverging configuration. A suture capturing mechanism formed on the jaw members securely captures suture to both push and pull the captured when the jaw assembly is retracted into the hollow distal tip. The device may also include a second suture capturing mechanism that loosely captures suture and enables the captured suture to slide.

18 Claims, 19 Drawing Sheets

(58) Field of Classification Search
CPC .......... A61B 17/00862; A61B 17/2943; A61B 17/2923; A61B 17/2926; A61B 18/1445
USPC ........................................................ 606/148
See application file for complete search history.

(56) References Cited

U.S. PATENT DOCUMENTS

| | | | |
|---|---|---|---|
| 5,222,977 A | 6/1993 | Esser | |
| 5,261,917 A | 11/1993 | Hasson et al. | |
| 5,318,589 A * | 6/1994 | Lichtman | A61B 17/29 600/564 |
| 5,342,389 A * | 8/1994 | Haber | A61B 17/0469 606/148 |
| 5,454,822 A * | 10/1995 | Schob | A61B 17/0469 112/169 |
| 5,632,751 A * | 5/1997 | Piraka | A61B 17/062 606/139 |
| 5,797,958 A * | 8/1998 | Yoon | A61B 17/122 606/139 |
| 5,817,111 A | 10/1998 | Riza | |
| 5,984,938 A * | 11/1999 | Yoon | A61B 17/12013 606/139 |
| 5,993,466 A * | 11/1999 | Yoon | A61B 17/062 606/144 |
| 6,616,683 B1 | 9/2003 | Toth et al. | |
| 8,496,656 B2 * | 7/2013 | Shields | A61B 18/1445 606/51 |
| 9,936,943 B1 * | 4/2018 | Mancini | A61B 17/0483 |
| 10,420,574 B2 * | 9/2019 | Thrasher, III | A61B 17/282 |
| 11,096,682 B2 | 8/2021 | Foerster et al. | |
| 2002/0183785 A1 | 12/2002 | Howell et al. | |
| 2004/0055608 A1 * | 3/2004 | Stevens | A61B 90/36 128/898 |
| 2004/0087967 A1 | 5/2004 | Schur et al. | |
| 2004/0172057 A1 | 9/2004 | Guillebon et al. | |
| 2004/0249393 A1 | 12/2004 | Weisel et al. | |
| 2005/0159763 A1 | 7/2005 | Mollenauer et al. | |
| 2007/0213767 A1 | 9/2007 | Ravikumar | |
| 2009/0062819 A1 | 3/2009 | Burkhart et al. | |
| 2010/0262181 A1 * | 10/2010 | Choi | A61B 17/0482 606/206 |
| 2012/0123448 A1 | 5/2012 | Flom et al. | |
| 2012/0143222 A1 | 6/2012 | Dravis et al. | |
| 2013/0030450 A1 | 1/2013 | Dreyfuss et al. | |
| 2013/0030462 A1 | 1/2013 | Keating et al. | |
| 2013/0116709 A1 | 5/2013 | Ziniti et al. | |
| 2013/0144315 A1 * | 6/2013 | Hart | A61B 17/0625 606/144 |
| 2013/0190782 A1 | 7/2013 | Nason | |
| 2013/0324803 A1 | 12/2013 | Mohajer | |
| 2015/0272603 A1 * | 10/2015 | Shelton, IV | A61B 17/2909 606/207 |
| 2016/0000423 A1 * | 1/2016 | Shields | A61B 17/062 606/147 |
| 2016/0022488 A1 | 1/2016 | Dimmig et al. | |
| 2016/0278801 A1 | 9/2016 | Michelini et al. | |
| 2017/0042533 A1 | 2/2017 | Lunn et al. | |
| 2017/0049465 A1 * | 2/2017 | Ravikumar | A61B 17/3417 |
| 2018/0116652 A1 | 5/2018 | Torrie | |
| 2019/0125384 A1 * | 5/2019 | Scheib | A61B 17/29 |
| 2019/0336124 A1 | 11/2019 | Pisarnwongs et al. | |

OTHER PUBLICATIONS

International Preliminary Report on Patentability dated Mar. 2, 2021 from PCT Application No. PCT/US2020/045998.
International Search Report & Written Opinion dated Nov. 23, 2020 from PCT Application No. PCT/US20/45998.
International Search Report & Written Opinion dated Oct. 9, 2020 from PCT Application No. PCT/US2020/070307.
European Search Report dated Dec. 20, 2021 from related Application No. EP19796675.7, 9 pages.
International Search Report & Written Opinion dated Dec. 14, 2021 from PCT Application No. PCT/US21/49936.

* cited by examiner ent applica-
SUTURE PASSING DEVICE

CROSS-REFERENCE TO RELATED APPLICATION(S)

This application is a continuation of U.S. patent application Ser. No. 16/400,681, filed May 1, 2019, which claims benefit of U.S. Provisional Application No. 62/667,021 filed on May 4, 2018, and U.S. Provisional Application No. 62/689,388 filed on Jun. 25, 2018, which are hereby incorporated by reference herein in their entirety.

BACKGROUND OF THE INVENTION

1. Field of the Invention

The present invention relates in general to medical devices. More particularly, the invention is directed to a suture passer.

2. Description of Prior Art and Related Information

Often times an important aspect of a surgical procedure is to pass suture through tissue. This could be required to mend a tear or connect two or more pieces of soft tissue. Though this task is common it can be challenging for the surgeon especially in an arthroscopic procedure where visualization is limited.

Many devices have been created to address difficult suturing scenarios but there are still certain procedures and anatomies where the average surgeon still struggles. For example, suturing the labrum at times can prove challenging particularly when the tissue is severely damaged. In such cases decreasing the overall profile of the feature penetrating the tissue and optimizing the working profile of the instrument to improve access to the working site can be critical factors to facilitate suturing.

Within this smaller needle profile, a mechanism must be housed that allows easy passing and retrieving of suture by the doctor in an arthroscopic atmosphere. With many devices currently on the market a very small loop of suture is provided during tissue passing such that the surgeon is challenged to hit the miniscule target and retrieve the suture.

A device is required that easily passes suture through tissue and provides a large amount of suture on the other side of the tissue that will be relatively easy for the surgeon to grab and pull out of the arthroscopic portal. This system must also be relatively simple so that the manufacturing cost can be kept at a reasonable level.

SUMMARY OF THE INVENTION

In one aspect, a suture passing device is provided. The device comprises a handle and a shaft coupled to the handle. The shaft comprises a sharp distal tip that defines a shaft axis. The shaft defines a lumen.

A jaw assembly is housed within the shaft. The jaw assembly comprises a first jaw member and a second jaw member. The first jaw member and the second jaw member are movable with respect to each other between a closed position and an open position. The jaw assembly comprising a push-pull suture capturing mechanism. An actuating mechanism is coupled to the jaw assembly and configured to move the jaw assembly between the closed position and the open configuration.

The first jaw member and the second jaw member are biased away from each towards the open position and moved to the open position when the actuator moves the jaw assembly distally with respect to the shaft such that first jaw member and the second jaw member each diverge from the shaft axis when exiting the shaft. The first jaw member and the second jaw member are moved to the closed position when the actuating mechanism is moved to retract the jaw assembly proximally with respect to the shaft.

The suture capturing mechanism may preferably comprise teeth. The suture capturing mechanism may comprise a first plurality of pointy teeth included in the first jaw member to form a first scalloped edge, and a second plurality of pointy teeth included in the second jaw member to form a second scalloped edge. The first plurality of teeth may preferably be nestable with the second plurality of teeth when the jaw assembly is in the closed configuration.

The shaft may comprise a bent shaft portion.

The sharp distal tip may comprise a blade tip at the distal end. A distal end of the jaw assembly may be retracted into the shaft in a preferred range of 10 mm to 45 mm from the blade tip.

The device may further comprise a stacked jaw assembly where a third jaw member stacked on and movable in unison with the first jaw, and a fourth jaw member stacked on and movable in unison with the second jaw.

The jaw assembly may further comprise a second loose suturing capturing mechanism.

The jaw assembly may further comprise a cutout proximal to the suture capturing mechanism.

The jaw assembly may preferably comprise a thickness in the range of 0.4 mm to 4.0 mm.

The jaw assembly comprises an exterior and the shaft comprises an interior shaft surface, and a gap between the exterior of the jaw assembly and the interior shaft surface is less than 1 mm.

In a further aspect, a suture passing device is provided having a jaw assembly comprising a push-pull suture passing mechanism. The device comprises a handle and a shaft coupled to the handle. The shaft comprises a sharp distal tip that defines a shaft axis. The shaft defines a lumen.

A jaw assembly is housed within the shaft. The jaw assembly comprises a first jaw member and a second jaw member. The first jaw member and the second jaw member are movable with respect to each other between a closed position and an open position.

An actuating mechanism is coupled to the jaw assembly and configured to move the jaw assembly between the closed position and the open configuration. The first jaw member and the second jaw member are biased away from each towards the open position and moved to the open position when the actuating mechanism moves the jaw assembly distally with respect to the shaft such that first jaw member and the second jaw member each diverge from the shaft axis when exiting the shaft. The first jaw member and the second jaw member are moved to the closed position when the actuating mechanism is moved to retract the jaw assembly proximally with respect to the shaft. The push-pull suture capturing mechanism comprises a set of teeth formed on at least one of the first jaw member and second jaw member.

The shaft may comprise a bent shaft portion.

The jaw assembly may comprise a second loose suturing capturing mechanism.

The jaw assembly may comprise a cutout proximal to the push-pull suture capturing mechanism.

The device may comprise a stacked jaw assembly where a third jaw member is stacked on the first jaw and a fourth jaw member is stacked on the second jaw. The third jaw and the fourth jaw preferably converge and diverge from each other in unison with the first jaw and second jaw.

In a further aspect, a suture passing device is provided having a stacked jaw assembly minimizing jaw movement within a shaft in which the jaw assembly is housed. The shaft is coupled to a handle. The shaft comprises a sharp distal tip that defines a shaft axis. The shaft defines a lumen. A dual-stack jaw assembly housed within the shaft comprises a first pair of jaw members and a second pair of jaw members stacked on the first pair of jaw members to form a first jaw member stack and a second jaw member stack. The first jaw member stack and the second jaw member stack are movable with respect to each other between a closed position and an open position. The jaw assembly comprises a push-pull suture capturing mechanism.

An actuating mechanism is coupled to the jaw assembly and configured to move the jaw assembly between the closed position and the open configuration. The first jaw member stack and the second jaw member stack are biased away from each towards the open position and moved to the open position when the actuating mechanism moves the jaw assembly distally with respect to the shaft such that first jaw a member stack and the second jaw member stack each diverge from the shaft axis when exiting the shaft. The first jaw member stack and the second jaw member stack are moved to the closed position when the actuating mechanism is moved to retract the jaw assembly proximally with respect to the shaft.

The first jaw member comprises a first set of teeth configured to capture suture and the second jaw member comprises a second set of teeth configured to capture suture.

The shaft comprises a cutout proximal to the jaw assembly.

The push-pull suture capturing mechanism preferably comprises a scalloped edge.

Methods of passing suture are also provided.

DETAILED DESCRIPTION OF THE PREFERRED EMBODIMENTS

The following preferred embodiments, in general, are directed to devices and methods for manipulating and passing suture. As will be appreciated, aspects of the suture passing device and its embodiments provide convenience for grasping suture and passing captured suture through tissue. Moreover, aspects disclosed are useful and superior to conventional suture passing devices because the preferred elements provide a reliable and more convenient capture of sutures. In general, preferred devices are disclosed which include a jaw assembly having a suture capturing mechanism that securely pushes and pulls a captured suture. It will be understood that the embodiments disclosed may include different jaw assemblies and suture capturing mechanisms in combination and no one jaw assembly is necessarily operated with any particular suture capturing mechanism disclosed. Thus, enumeration in the following does not imply that a jaw assembly with the same number series must be operated by a suture capturing mechanism of the same number series.

Figure 1:
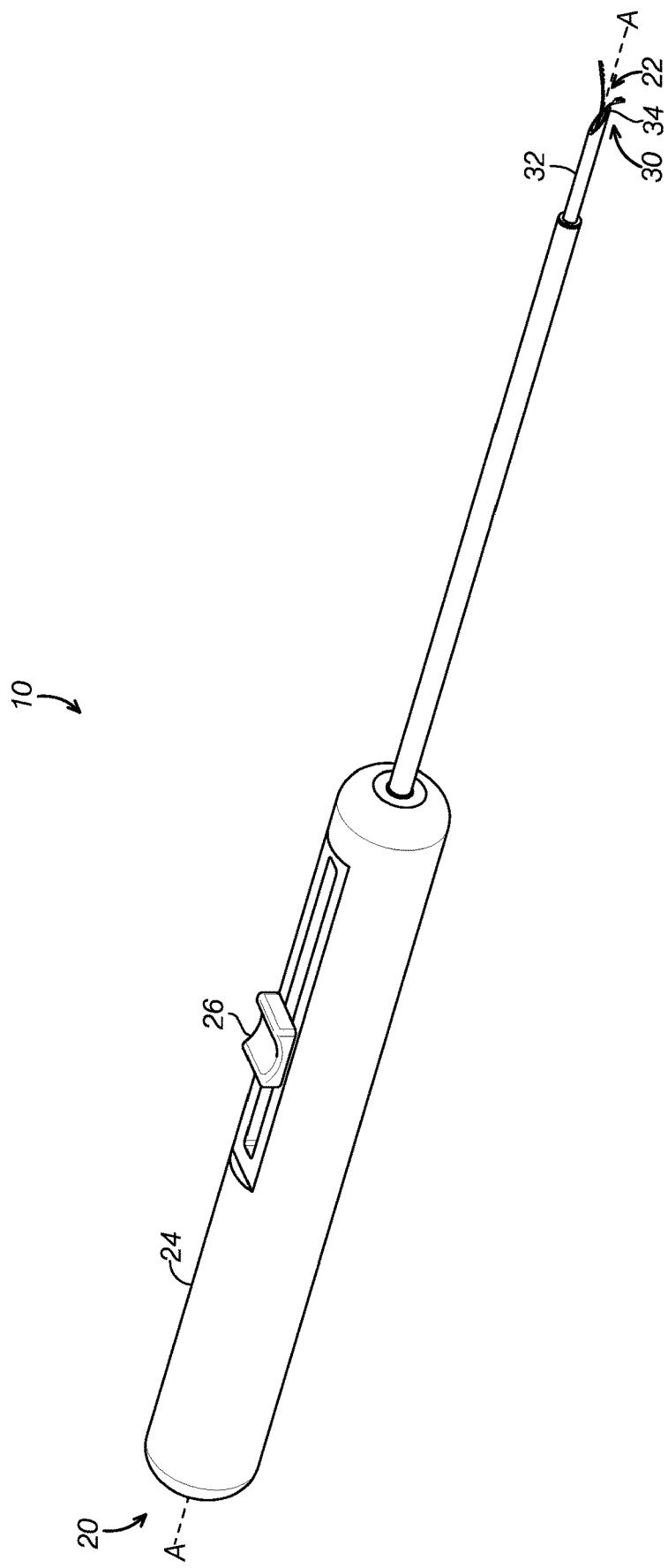
FIG. 1 is a top perspective view of a suture passing device according to first preferred embodiment.

Referring now to FIG. 1, a first preferred embodiment of a suture passing device or suturing device 10 is shown. The device 10 preferably comprises a proximal portion 20 and a distal portion 22. The proximal portion 20 includes a handle 24 and an actuating mechanism which may comprise a thumb slide 26. The thumb slide 26 communicates with and actuates a jaw assembly 30 included in the distal portion 22 of the device 10. An actuator (not shown) is coupled to the thumb slide 26 and the jaw assembly 30 which is housed in a shaft 32. The shaft 32 defines a shaft axis A.

The device 10 comprises a distal tip 34. In the preferred embodiment, the distal tip 34 comprises a sharp needle tip. While the distal tip 34 is shown in a straight configuration for simplicity, it should be expressly understood that this tip can be bent in a number of different curves as required.

Figure 2A:
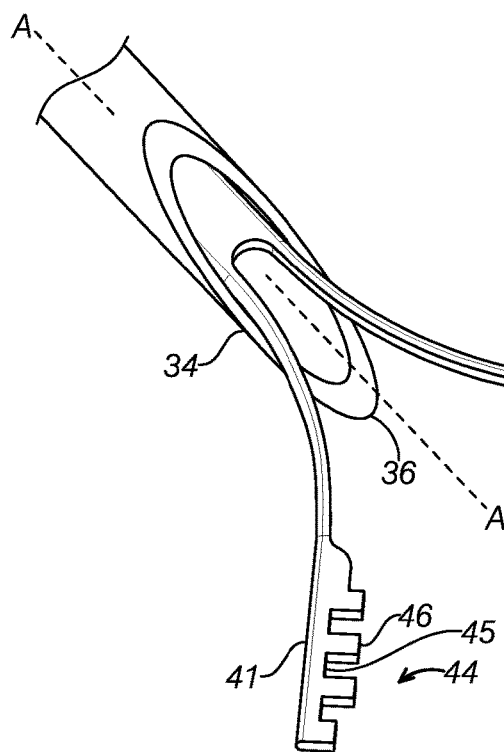
FIG. 2A is a perspective view of the first preferred embodiment of the suture passing device with jaw assembly in an open configuration.

In FIG. 2A, a close-up of the first preferred distal needle tip 34 is shown with the jaw assembly 30 in a default open configuration when the actuating mechanism 26 of FIG. 1 is moved distally. The distal tip 34 may comprise a sharpened distal blade that enhances its ability to puncture tissue. In the first preferred embodiment, the jaw assembly 30 preferably comprises a pair of jaw members, or first and second jaw members, 41. In the preferred embodiment, the full length of the first and second jaw members 41 can range from 2 mm to 15 mm or longer depending on the amount of spread and reach desired for suture manipulation.

The jaw assembly 30 comprises a push-pull suturing capturing mechanism 44 preferably formed on the pair of jaw members 41. In the first preferred embodiment, the suture capturing mechanism 44 may comprise a series of valleys 45 and teeth 46 formed on each jaw member 41 in a preferably alternating pattern. In the preferred embodiment, the height of the teeth 46, or depth of the valleys 45 can range from 0.1 mm to 5 mm depending on the constraining tube diameter and suture to be manipulated. The number of valleys 45 and teeth 46 can vary from one to multiple quantities. The number of valleys 45 need not match the number of teeth 46. And the configuration on one jaw member 41 relative to the other opposite jaw member 41 can mesh as shown in the illustrated embodiment, comprise a mirror image (which would not mesh) or interact in a more random manner. Each jaw member 41 can also have a different pattern relative to the other jaw member 41 such as staggered teeth. As a further example, one jaw member 41 may comprise a flat face, i.e. no valleys or teeth, while the opposite jaw member 41 comprises valleys and teeth.

In the preferred embodiment, the push-pull suture capturing mechanism 44 is configured to both push and pull a captured portion of suture. The suture capturing mechanism 44 may accomplish this dual push-pull action by having, for example, teeth 46 that affix to and lock on a specific point of suture. That fixed point of suture may be both pulled—e.g., when the jaw assembly 30 is retracted into the into hollow shaft 32—and pushed—e.g., when the jaw assembly 30 exits out the shaft carrying the affixed point of suture until the jaw members 41 diverge from each other so as to release the suture.

In the preferred embodiment, the jaw assembly 30 may preferably be composed of a variety of materials including plastic and/or metal. One preferred material may be Nitinol which can be shape-set in the spread-out configuration as shown in FIG. 2A. In the illustrated embodiment, the jaws may be preconfigured to a default spread-apart configuration shown in FIG. 2A when at rest and can be brought together as in FIG. 2D without yielding the material. In the first preferred embodiment, there are no hooks located at the distal ends of the jaws.

In the default open position of the jaw assembly 30 as shown in FIG. 2A, the first and second jaws 41 diverge away from the shaft axis A, and thus diverge away from each other 41. When the jaws 41 are moved distally to exit the distal tip 34, the jaws 41 are biased to this flared-out open configuration where neither jaw 41 is parallel to the shaft axis A.

Figure 2B:
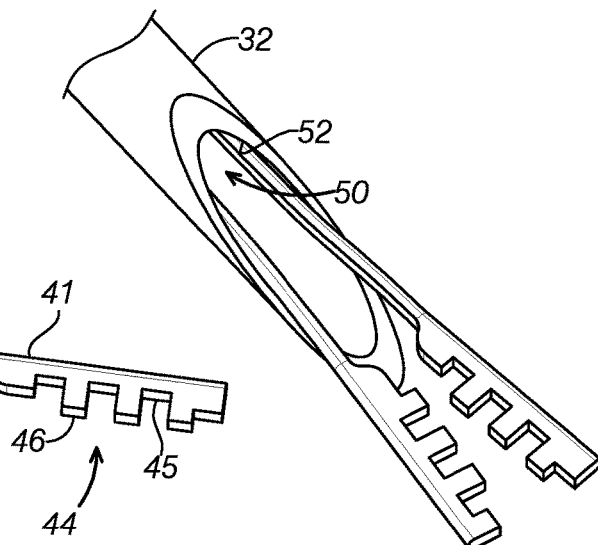
FIG. 2B is a perspective view of the first preferred embodiment of the suture passing device with jaw assembly in a partially retracted configuration.
Figure 2C:
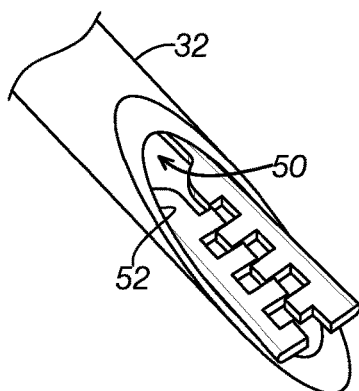
FIG. 2C is a perspective view of the first preferred embodiment of the suture passing device with jaw assembly in a further retracted configuration.
Figure 2D:
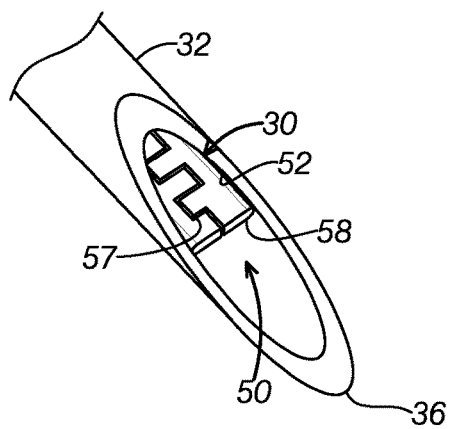
FIG. 2D is a perspective view of the first preferred embodiment of the suture passing device with jaw assembly in a retracted, closed configuration.

In FIGS. 2B, 2C, and 2D, the jaw assembly 30 is being drawn in to a lumen 50 defined within the shaft 32 when the actuating mechanism 26 shown in FIG. 1 is moved proximally. As shown in FIG. 2B, an inner wall 52 of the shaft 32 slowly forces the two jaw members 41 together as the jaw assembly 30 is retracted into the distal tip 34 and further into the shaft 32. The inner wall 52 causes the pair of jaw members 41 to converge towards each other as the jaw assembly 30 is drawn into lumen 40. In FIG. 2D, the jaw assembly 30 is retracted into distal tip 34 and moved to a closed configuration when the actuating mechanism is moved further proximally. The inner wall 52 is preferably abutting not only one jaw member 41, but both jaw members 41 to cause the pair of jaw members 41 to converge when retracted into the shaft 32. This is accomplished in part to the default shape of each jaw 41 which is preferably biased away (i.e., opposite direction) from the opposing jaw 41 as shown in FIG. 2A.

In the first preferred embodiment where similar geometries are formed on each jaw member 41, this convergence can be likened to two sets of teeth meshing in a zipper-type action when retracted into the shaft 32. In the illustrated embodiment, it should be noted that the jaw members 41 are shown coming together on the same plane but it is a common occurrence for jaw members 41 to come in to the distal tip 34 at slightly different planes especially if suture is also being pulled in. Also, the two jaw members 41 not need be symmetrical. For example, one jaw member could be curved as shown and the other jaw member relatively straight.

In the preferred embodiment shown in FIG. 2D, the device 10 comprises a kerf 57 that forms a space between the two jaw members 41 which can vary from touching to a distance capable of holding a particular suture of a desired size. This gap can be as large as 0.5 mm and still hold some of the larger suture sizes. For smaller suture sizes this gap will often be closer to a range between 0 mm and 0.25 mm. In the preferred embodiment, the distal end 58 of the jaw assembly 30 may be retracted into the shaft 32 in a preferred range of 10 mm to 45 mm from the blade tip 36.

Figure 3A:
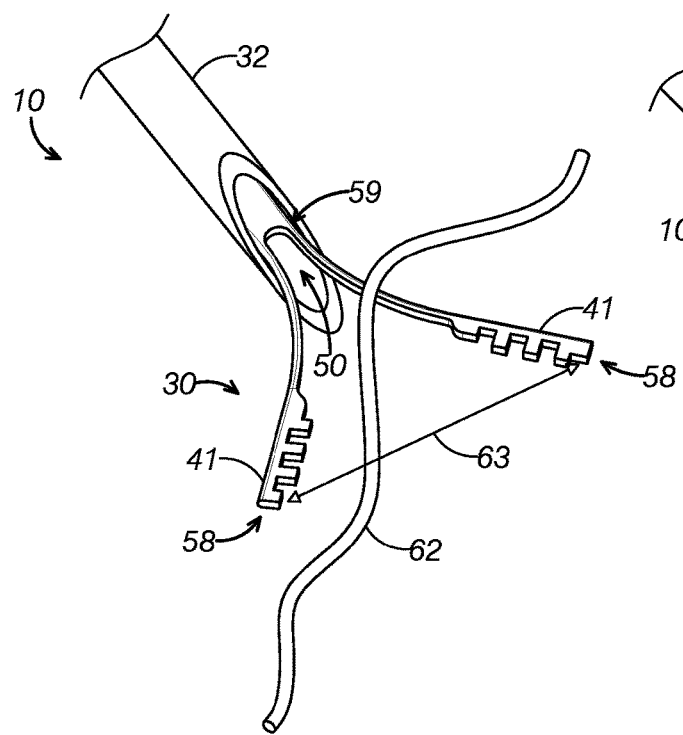
FIG. 3A is a perspective view of the first preferred embodiment of the suture passing device with jaw assembly in an open configuration to receive suture.

FIGS. 3A-3D illustrate operative views of the preferred suturing device 10. FIG. 3A shows the deployed jaw assembly 30 extending distally out from the shaft 32 and surrounding a piece of suture 62 with a wide capture space, or region 63 that is generally shaped as a flared-out funnel or flared-out horn. In this deployed configuration, the jaw members 41 are extended distally out of the shaft 32 and positioned on opposite sides of the suture 62 in their default divergent configuration. The jaw members 41 are biased to a diverging configuration when deployed and moved to a converging configuration when retracted into the tube 32. The spread of the distal jaw tips 43 will be dependent on what the nearby anatomy of the patient will allow, but the ability to spread between 5 and 10 mm will be desired in most instances. In this default diverging configuration shown in FIG. 3A, the jaw members 41 are preferably flared out such that the distance between counterpart portions of the jaw members 41 increases starting from the proximal jaw portion 59 to the distal jaw portion 58. This flared-out configuration between the jaw members 41 creates a wide capture space for receiving a suture to be captured.

Figure 3B:
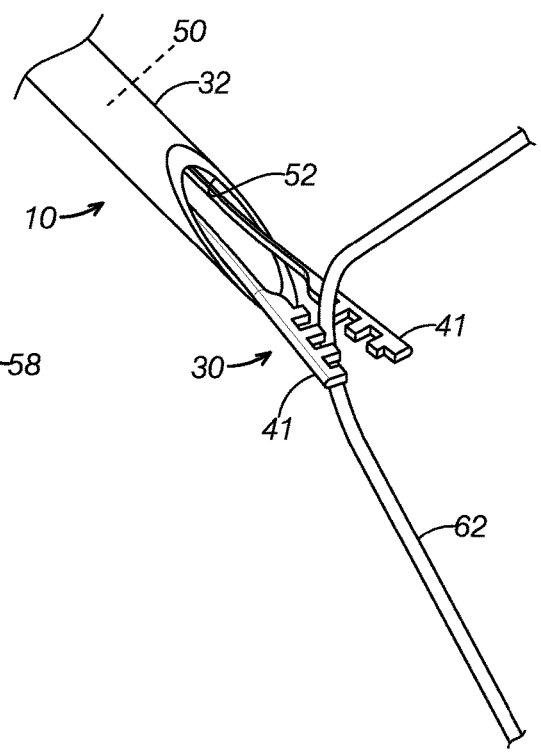
FIG. 3B is a perspective view of the first preferred embodiment of the suture passing device with jaw assembly in a partially retracted configuration to begin grasping suture.
Figure 3C:
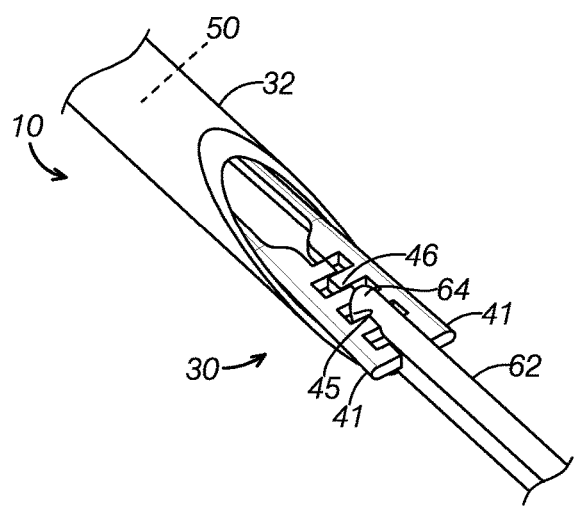
FIG. 3C is a perspective view of the first preferred embodiment of the suture passing device with jaw assembly in a closed configuration to capture suture.

In FIG. 3B, the jaw assembly 30 is partially drawn into the shaft 32 which pushes the jaw members 41 towards each other to capture the suture 62. In particular, the inner wall 52 of the shaft 32 causes the jaws 41 to converge as the jaw assembly 30 is retracted into the lumen 50. The suture 62 is retracted further in FIG. 3C which illustrates a closed configuration of the jaw assembly 30 wherein the jaws 41 abut each other. In this closed position in FIG. 3C, the suture 62 is captured as a fixed point 64 of suture 60 is locked between the valleys 45 and teeth 46 of the jaw members 41. In the preferred embodiment, the captured portion of suture 62 may be retracted into the lumen 50 in a preferred range of 10 mm to 45 mm from the distal tip 34.

Figure 3D:
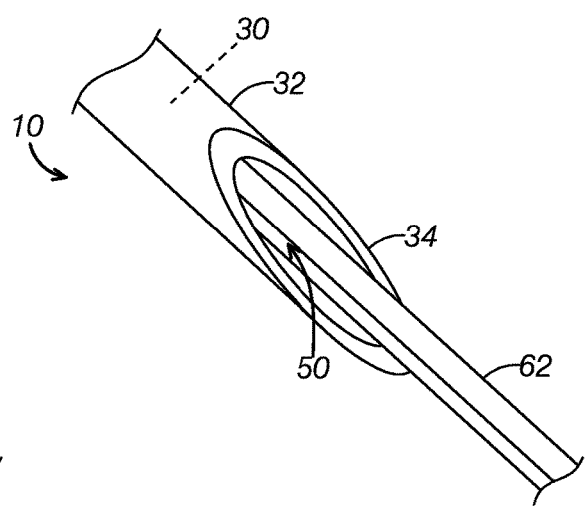
FIG. 3D is a perspective view of the first preferred embodiment of the suture passing device with jaw assembly in a fully retracted, closed configuration carrying suture within the distal tip.

In FIG. 3D, the closed jaw assembly is further retracted into the shaft 32 carrying the suture 62 further within the distal tip 34. It should be noted that the suture 62 can be pulled in a relatively long distance such that when the suture 62 is pushed out, a large loop can be formed with the deployed length. This length could be 10 mm to 45 mm, or more. The captured suture portion 62 is pushed out by virtue of the suture capturing mechanism (disposed within the shaft in FIG. 3D) locking onto a fixed point of suture and carrying the affixed point of captured suture in a distal direction. This push dynamic is distinguishable from prior art jaw assemblies that loosely hook onto a suture and thus cannot distally push a fixed point of suture.

Figure 4A:
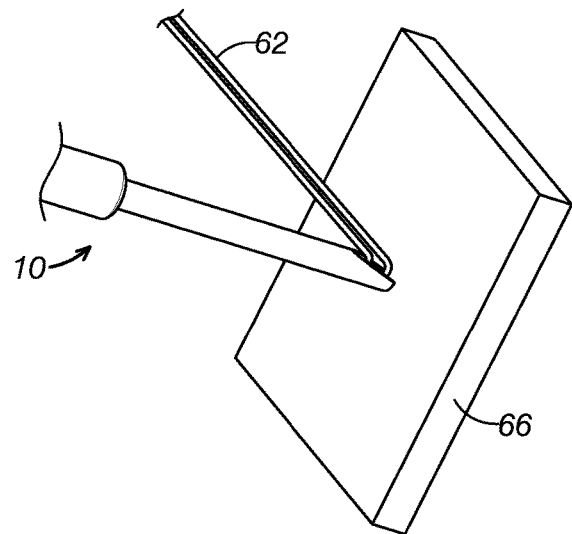
FIG. 4A is a perspective view of the first preferred embodiment of the suture passing device carrying suture prior to penetrating tissue.
Figure 4B:
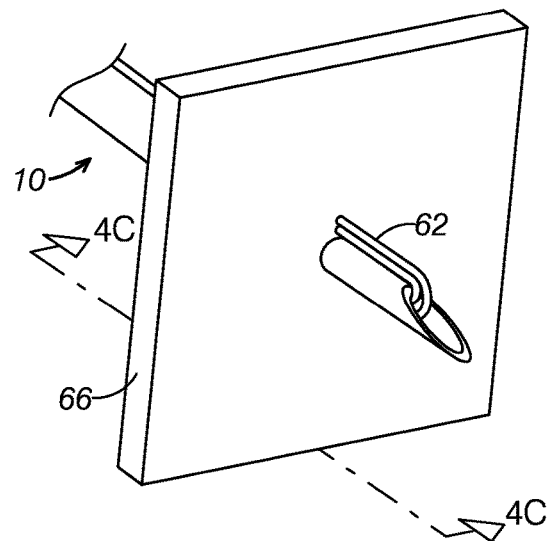
FIG. 4B is a perspective view of the first preferred embodiment of the suture passing device penetrating tissue with the carried suture.

FIGS. 4A-4E show a preferred method for passing suture 62 with the first preferred embodiment of the suturing device 10. In FIG. 4A, the suture 62 has been loaded in the passer 10 as shown in FIG. 3D. In FIG. 4B, the sharp distal tip 34 is pushed through the tissue 66 carrying at least portion of suture 62 through the tissue 66.

Figure 4D:
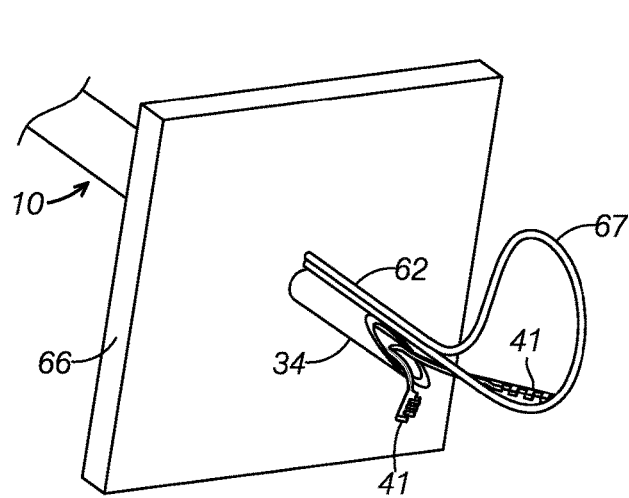
FIG. 4D is a perspective view of the first preferred embodiment of the suture passing device releasing suture after being carried through tissue.
Figure 4E:
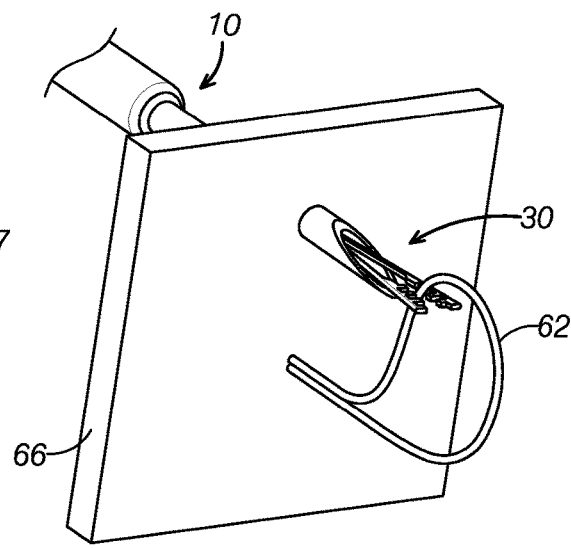
FIG. 4E is a perspective view of the first preferred embodiment of the suture passing device penetrating tissue to grasp a loop section of the suture.
Figure 4C:
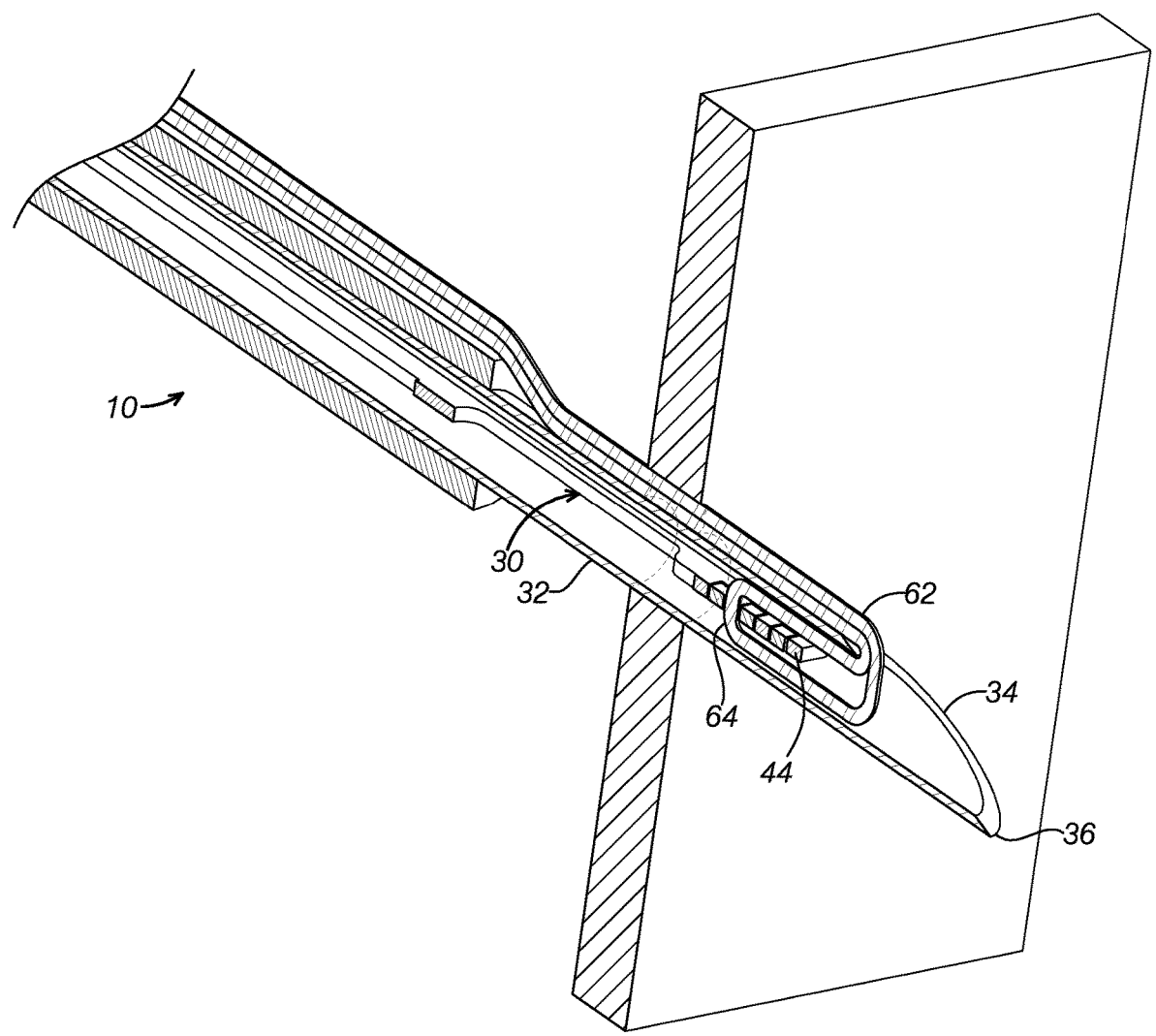
FIG. 4C is a cross-sectional perspective view showing the first preferred embodiment of the suture passing device in the position illustrated in FIG. 4B.

In the retracted position shown in FIG. 4C, the jaw assembly 30 carries the captured suture portion 62 into the shaft 32 for a preferred distance in the range of 10 mm to 45 mm measured from the blade tip 36 end of the distal tip 34. In the preferred embodiment, the suture capturing mechanism 44 locks onto a fixed point 64 of suture 62 and distally pushes this affixed point 64 of suture 62 when the jaw assembly 30 is translated distally with respect to the shaft 32. Jaw mechanisms configured to lock onto a fixed point of suture may comprise teeth/valley combinations as discussed above, and a variety of gripping or securing jaw combinations as discussed below in reference to FIGS. 8A-31, except FIG. 14.

In FIG. 4D the jaw assembly 30 is deployed out the tip 34 so that the jaw members 41 push and pull the suture 62 out of the tip 34 and release a large suture loop 67 once the proper spread is achieved between the jaw members 41. This leaves the large loop 67 that can easily be grabbed by the passer 10 once it has adjusted to a new position as shown in FIG. 4E. It should be noted that an addition or variation to this method is to pierce the tissue 66 with a distal tip 34 that is not loaded with suture. The jaw assembly 30 can then grab the suture 62 on the other side of the tissue 66 similar to FIG. 4E.

Figure 5A:
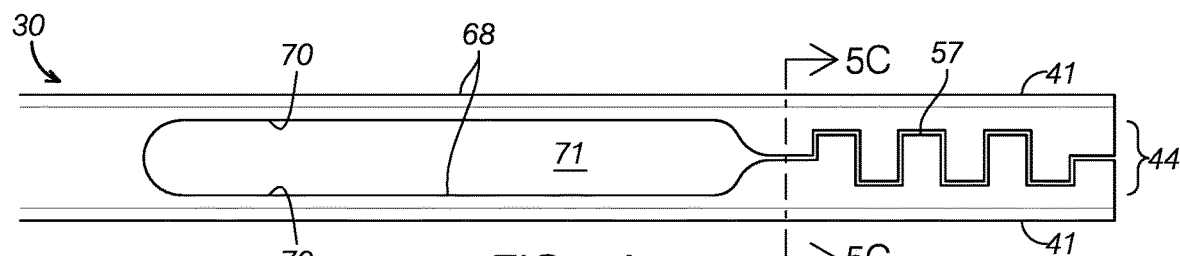
FIG. 5A is a top plan view of the first preferred jaw assembly.

FIG. 5A illustrates details of the preferred jaw assembly 30 having a suture capturing mechanism 44 that prevents or inhibits captured suture from sliding. For machining purposes there may be a witness kerf 57. This acts to form the pattern of teeth 45 and valleys 46 between the two jaw members though the two jaws do not necessarily have to nest as shown in the illustrated embodiment. Also, the kerf 57 can vary in width over its length to create smaller or larger gaps between the two jaws 41.

In FIG. 5A, the jaw assembly 30 may preferably comprise thinned sections 68 with cutouts 70 that allow for the pair of jaws 41 to bend outwards away from each other bend outwards (as shown in FIG. 3A) or inwards with minimal imparted stresses as shown in FIG. 3A. This diverging motion is represented in FIG. 5C with movement arrows 79 indicating that the jaw assembly 30 as a whole is more flexible along the plane shown in FIG. 5C. The thinned sections 68 shown in FIG. 5A also provide greater flexibility for the jaw assembly 30 to bend as indicated by the movement arrows 77 in FIG. 5B. The thinned sections 68 also allow for twisting of the jaw assembly 30 under torsion forces, thereby allowing the jaw assembly 30 to pass through non-linear tubes that may be bent in multiple planes. Referring back to FIG. 5A, the thinned sections 68 are preferably located proximal to suture capturing mechanism 44 and collectively form a void 71 when the suture capturing mechanism is in the closed position as shown. For proper flexibility without imparting yielding stresses, the length and displacement must be taken into account but in general the thickness can preferably range from 0.2 mm to 2 mm.

And for jaw assemblies 30 composed of memory materials such as Nitinol the thinned sections 68 allow for shape set in an open position. The proximal relief is a feature that minimizes the stress on the part when the jaw members 41 are displaced. In the first preferred embodiment, the jaw members 41 preferably comprise distal portions of a unitary jaw structure 30. Thinned sections 68 are shown to have uniform cross section along their length but this cross-section area may vary over that length in order to evenly distribute stresses during bending. For instance, the cross-sectional area of the thinned section 68 can decrease as it gets closer to the teeth 46 in a way to even out stresses during bending.

Figure 5B:
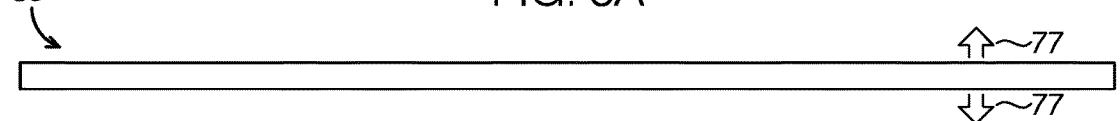
FIG. 5B is a side elevation view of the first preferred jaw assembly.
Figure 5C:
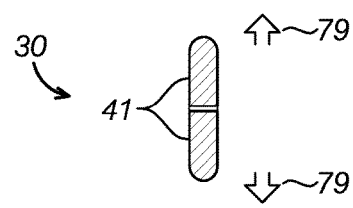
FIG. 5C is a cross-sectional view of the first preferred jaw assembly taken along lines 5C-5C of FIG. 5A.

A 90° view of FIG. 5A is shown in FIG. 5B. It is obvious that this aspect is much thinner than that of FIG. 5A which allows for relative flexure ease as shown with arrows 77 while minimizing imparted stresses. Another view of the relative planar thicknesses is shown in FIG. 5C.

In the following alternative embodiments, elements of similar structure are designated by the same reference numerals followed by at least one lower case letter (e.g., jaw assembly 30*b*)

FIGS. 6-10E illustrate alternative embodiments of the jaw assembly, each having a preferred suture capturing mechanism configured to lock onto a point of suture and both push and pull the affixed point of suture.

Figure 6:
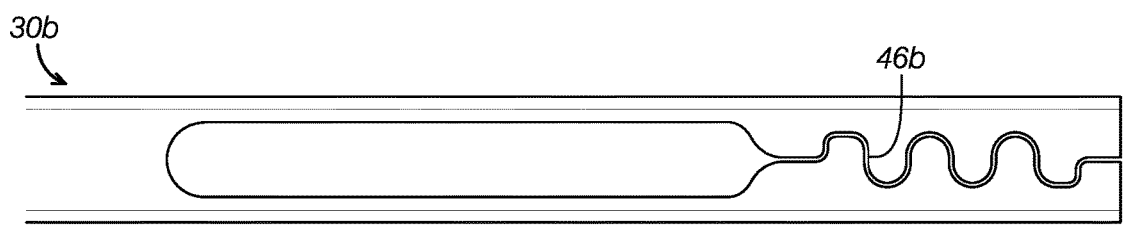
FIG. 6 is a top plan view of an alternative embodiment of a jaw assembly.

FIG. 6 shows an alternative embodiment of the jaw assembly 30*b* comprising teeth 46*b* that need not be rectangular but can be curved or round as shown. The teeth can also be triangular, or a combination of different shapes as shown in the following embodiments.

Figure 7:
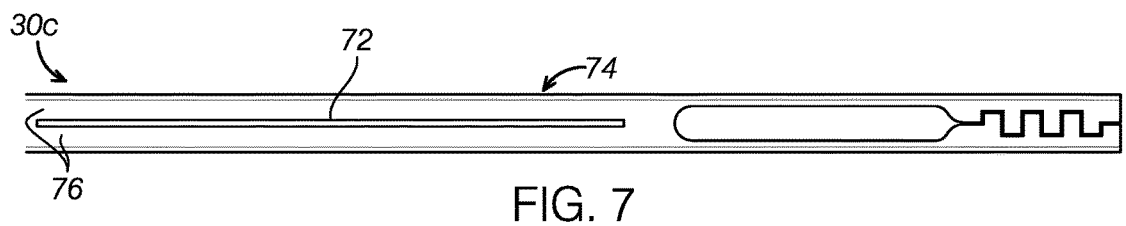
FIG. 7 is a top plan view of a further alternative embodiment of a jaw assembly.

FIG. 7 illustrates a jaw assembly 30*c* comprising an axial slit 72 that makes the jaw ribbon 74 more flexible. This allows for the two halves 76 of the ribbon 74 to move independently while keeping most of the compressive and tensile properties of the ribbon 74. This becomes most important when the ribbon 74 is moving through constraining components that have bends in multiple axis.

Figure 8A:
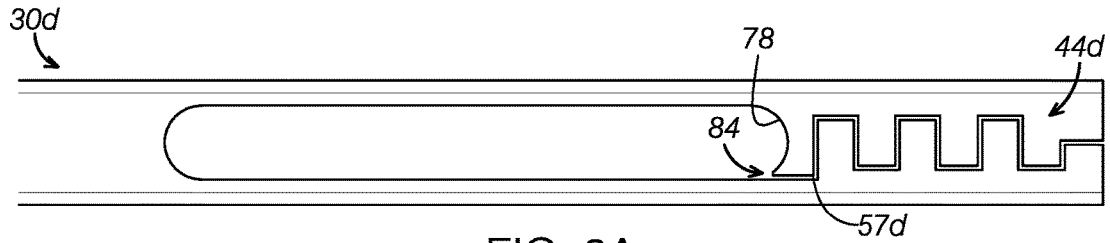
FIG. 8A is a top plan view of a further alternative embodiment of a jaw assembly.

FIG. 8A illustrates a jaw assembly 30*d* having a second suture capture mechanism 78 that enables suture to slide once it has been captured. The gentle geometry of the cutout distal curve 78 can be positioned such that the suture captured by the jaw assembly 30*d* will slide within the curve 78 when the device pulls on the suture. In the configuration shown, access 84 to the kerf 57*d* is proximal to the distal-most portion 82 of the curve 78 such that the suture would tend to settle in to the curve 78 when the suture is moved distally with respect to the jaw assembly 30*d* (i.e., when the jaw assembly 30*d* is retracted proximally). This prevents the suture from getting stuck in the kerf access 84. The cutout distal curve 78 thus comprises a hook 78 that enables captured suture to slide transversely (i.e., in and out of the page in the view of FIG. 8A) with respect to the jaw assembly 30*d*. Thus, the jaw assembly 30*d* comprises two suture capture mechanisms 44*d*, 78: namely, a first push-pull suture capturing mechanism 44*d* that locks onto a fixed point of suture and a second loose suture capturing mechanism 78 that captures suture while allowing the capture suture to slide.

Figure 8B:
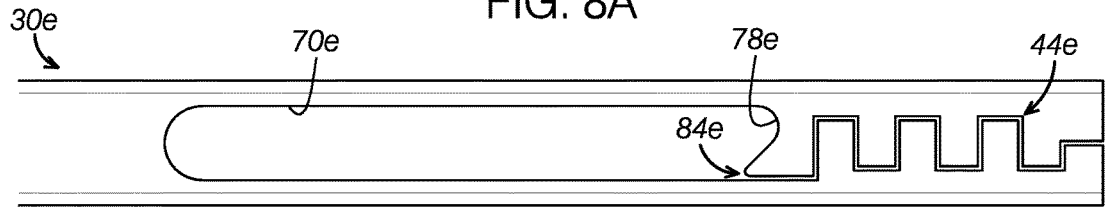
FIG. 8B is a top plan view of a further alternative embodiment of a jaw assembly.

In FIG. 8B, the cutout 70*e* of the jaw assembly 30*e* defines a distal cutout curve, or hook, 78*e* positioned even more distally with respect to the kerf access 84*e*. In comparison to the jaw assembly 30*d* shown in FIG. 8A, the kerf access 84*e* in FIG. 8B is positioned more proximally with respect to the hook 78*e*. The jaw assembly 30*e* thus comprises a first push-pull suture capturing mechanism 44*e* that locks onto a fixed point of suture and a second loose suture capturing mechanism 78*e* that allows captured suture to slide.

Figure 8C:
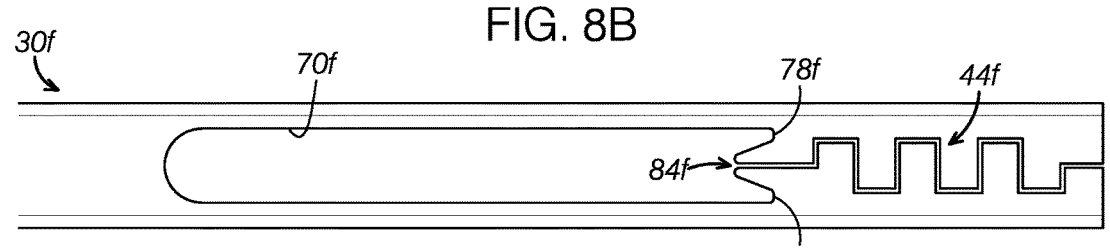
FIG. 8C is a top plan view of a further alternative embodiment of a jaw assembly.

In FIG. 8C, the cutout 70*f* of the jaw assembly 30*f* defines two distal cutout curves, or hooks, 78*f* positioned distally to the kerf access 84*f*, which enables the captured suture to seat in to either of the hooks 78*e* and away from the kerf access 84*f*. The jaw assembly 30*f* thus comprises a first push-pull suture capturing mechanism 44*f* that locks onto a fixed point of suture and a second loose suture capturing mechanism 78*f* having two hooks that allow captured suture to slide.

Figure 9A:
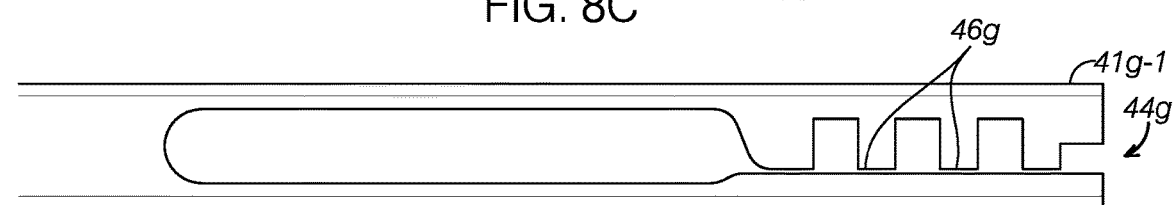
FIG. 9A is a top plan view of a further alternative embodiment of a jaw assembly.
Figure 9B:
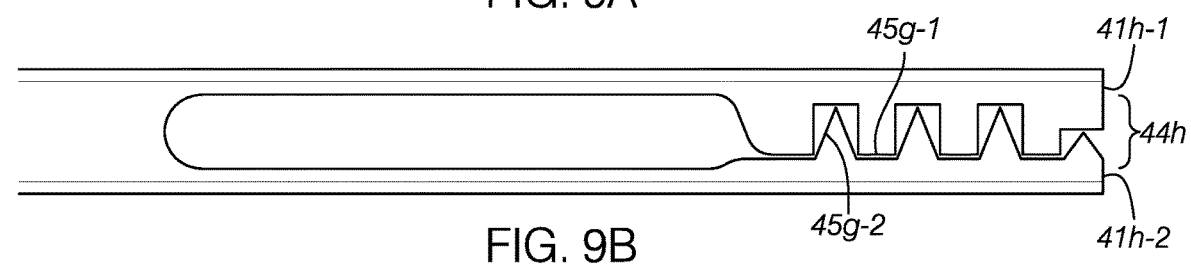
FIG. 9B is a top plan view of a further alternative embodiment of a jaw assembly.
Figure 9C:
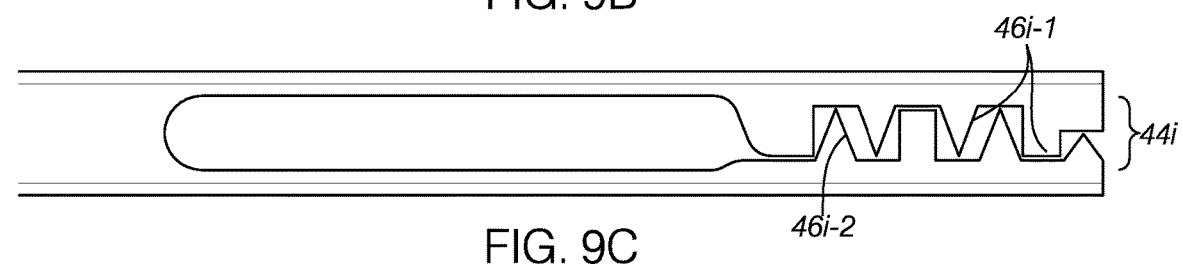
FIG. 9C is a top plan view of a further alternative embodiment of a jaw assembly.

FIGS. 9A-9C show alternative embodiments of the push-pull suture capturing mechanism having asymmetrical patterns of teeth and valleys, namely, where the pattern on a first jaw is not symmetrical to the pattern on the opposing second jaw. The teeth themselves can have a consistent or varying width and height along the length of the jaws. The number of teeth can also vary from one to more than one.

In FIG. 9A, the suture capturing mechanism 44*g* may comprise teeth 46*g* on only one jaw 41*g*-1 with the second jaw 41*g*-2 having a relatively flat jaw surface 86.

In FIG. 9B, the suturing capturing mechanism 44*h* comprises a first jaw 41*h*-1 with a first geometry of teeth 45*g*-1 while a second jaw 41*h*-2 comprises a different second geometry of teeth 45*g*-2.

In FIG. 9C, the suturing capturing mechanism 44*i* comprises different tooth geometries within the same jaw 41*i*-1, 41*i*-2. For example, the first jaw 41*i*-1 may have both rectangular and triangular teeth 46*i*-1. Similarly, the second jaw 41*i*-2 may itself have differently shaped teeth.

Figure 10A:
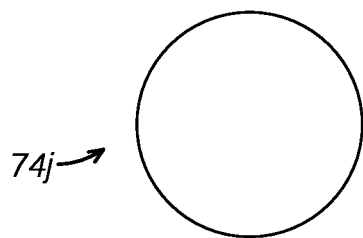
FIG. 10A is a cross-sectional view of an alternative embodiment of a ribbon of a jaw assembly.
Figure 10B:
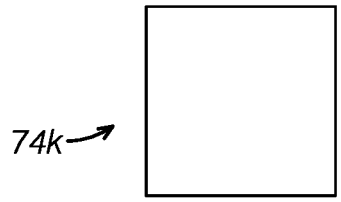
FIG. 10B is a cross-sectional view of an alternative embodiment of a ribbon of a jaw assembly.
Figure 10C:
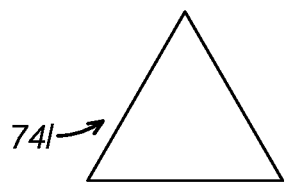
FIG. 10C is a cross-sectional view of an alternative embodiment of a ribbon of a jaw assembly.
Figure 10D:
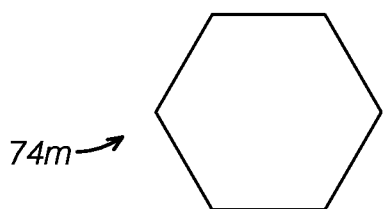
FIG. 10D is a cross-sectional view of an alternative embodiment of a ribbon of a jaw assembly.
Figure 10E:
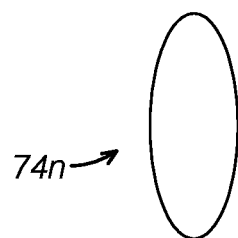
FIG. 10E is a cross-sectional view of an alternative embodiment of a ribbon of a jaw assembly.

FIGS. 10A-11B illustrate different cross-sectional profiles of preferred ribbons. FIG. 10A shows a ribbon 74*j* having a circular profile. FIG. 10B illustrates a ribbon 74*k* having a rectangular profile, which may comprise a square. FIG. 10C illustrates a ribbon 74*l* with a triangular profile. FIG. 10D illustrates a ribbon 74*m* having a hexagonal profile. FIG. 10E illustrates a ribbon 74*n* having an oval profile.

Figure 11A:
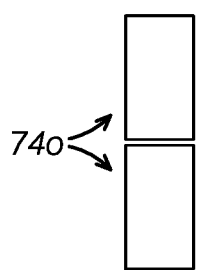
FIG. 11A is a cross-sectional view of an alternative embodiment of a ribbon of a jaw assembly.
Figure 11B:
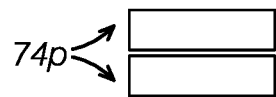
FIG. 11B is a cross-sectional view of an alternative embodiment of a ribbon of a jaw assembly.

FIG. 11A shows an assembly of two ribbons 74*o* stacked on top of each other lengthwise. FIG. 11B shows an assembly of two ribbons 74*p* stacked on top of each other widthwise.

Figure 12:
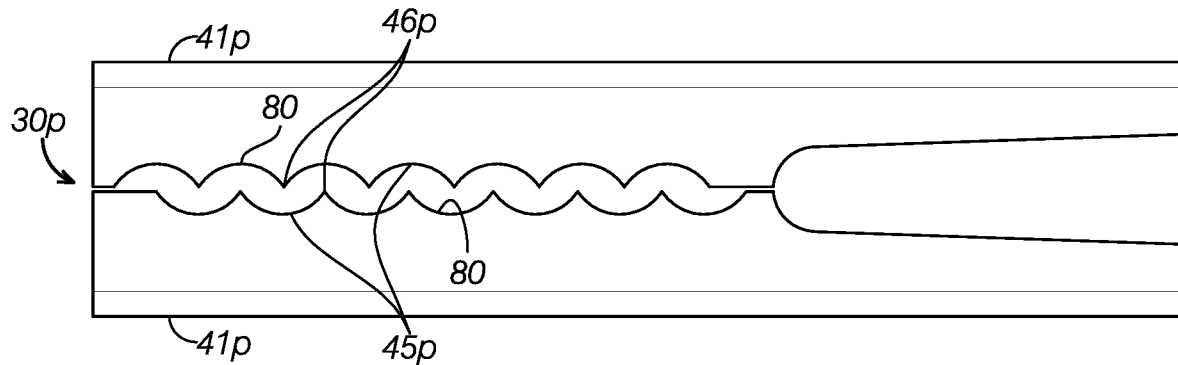
FIG. 12 is a top plan view of an alternative embodiment of a jaw assembly.

FIG. 12 illustrates a preferred jaw assembly 30*p* where each jaw 41*p* comprises an alternating pattern of pointy teeth 46*p* and curved valleys 45*p* to form a scalloped edge 80. In FIG. 12, the two scalloped edges 41*p* are staggered with respect to each other so as to nest at least slightly when the jaws 41*p* are closed.

Figure 13:
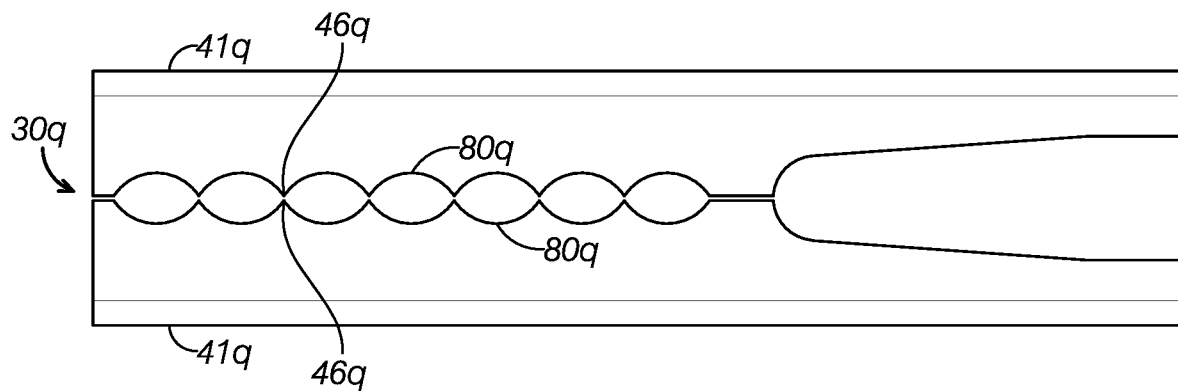
FIG. 13 is a top plan view of an alternative embodiment of a jaw assembly.

FIG. 13 illustrates a pair of jaws 41*q* with symmetrical scalloped edges 80*q* such that opposing pointy teeth 46*q* contact each other when the pair of jaws 41*q* is closed.

Figure 14:
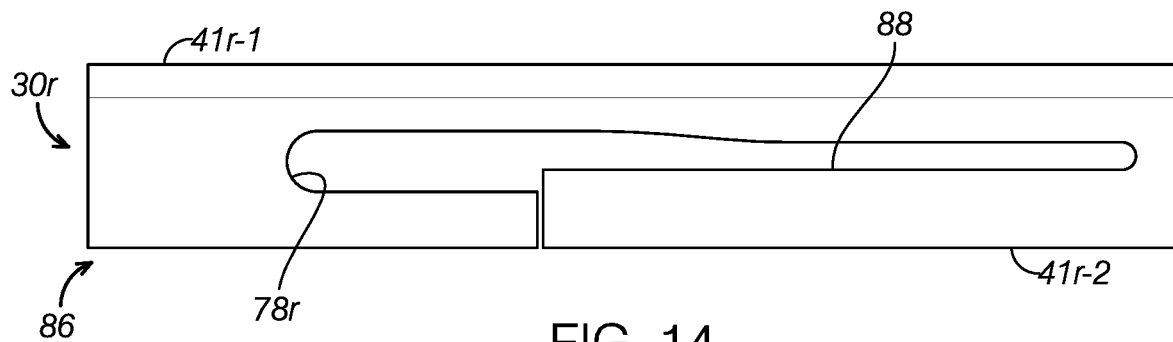
FIG. 14 is a top plan view of an alternative embodiment of a jaw assembly.

FIG. 14 illustrates a jaw assembly 30*r* where a first jaw 41*r*-1 comprises a distal U-shaped hook structure 86 that defines a hook 78*r* located distally to a distal end of the second jaw 41*r*-2 which comprises a substantially flat surface 88. This illustrated embodiment 30*r* would allow captured suture to slide.

Figure 15:
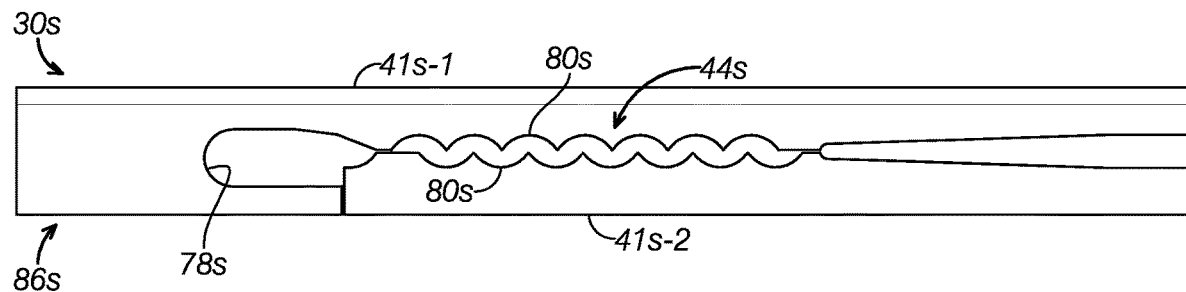
FIG. 15 is a top plan view of an alternative embodiment of a jaw assembly.

FIG. 15 illustrates a jaw assembly 30*s* where a first jaw 41*s*-1 comprises a distal U-shaped hook structure 86*s* that defines a hook 78*s* located distally to a distal end of the second jaw 41*s*-2. Each jaw 41*s*-1, 41*s*-2 comprises a scalloped edge 80*s* that is preferably staggered with respect to the opposite edge. The jaw assembly 30*s* thus comprises a first push-pull suture capturing mechanism 44*e* that locks onto a fixed point of suture and a second loose suture capturing mechanism 78s that allows captured suture to slide. In the preferred embodiment of FIG. 15, the loose suture capturing mechanism 78s is preferably distal to the fixed suture capturing mechanism 44s.

In any of the preferred embodiments disclosed herein having a loose suture capturing mechanism, it may be preferable to bring the loosely captured suture into the hollow shaft a preferred distance of 1 mm to 15 mm from a blade tip of the distal tip.

Figure 16:
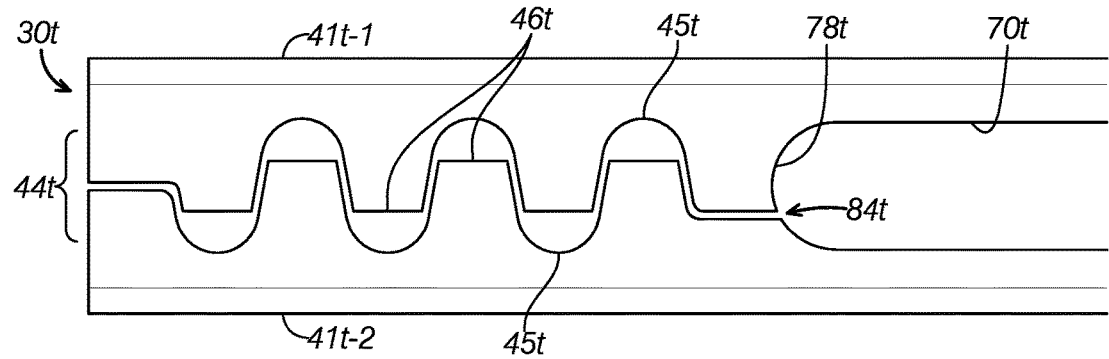
FIG. 16 is a top plan view of an alternative embodiment of a jaw assembly.

FIG. 16 illustrates a jaw assembly 30t where each jaw 41t comprises tapered teeth 46t and valleys 45t with curved bases 90. A cutout 70t located proximal to the suture capturing mechanism 44t defines a hook 78t positioned distal to the kerf access 84t. The jaw assembly 30t thus comprises a first push-pull suture capturing mechanism 44t that locks onto a fixed point of suture and a second loose suture capturing mechanism 78t that allows captured suture to slide. In the preferred embodiment of FIG. 16, the loose suture capturing mechanism 78t is preferably proximal to the fixed suture capturing mechanism 44t.

Figure 17:
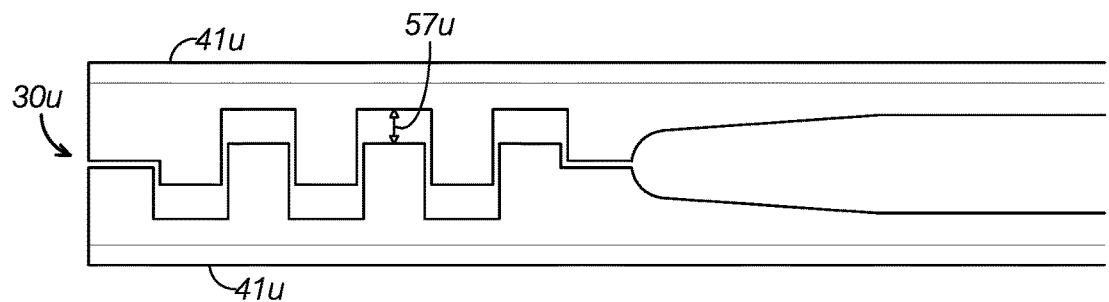
FIG. 17 is a top plan view of an alternative embodiment of a jaw assembly.

FIG. 17 illustrates a jaw assembly 30u where each jaw 41u comprises tapered teeth 46u and valleys 45u spaced apart from the counterpart teeth 46u and valleys 45u on the opposite jaw 41u so as to form a larger kerf 57u, namely, a greater gap or space between the medial edge of a tooth 46t and the base of the corresponding valley 45u.

Figure 18:
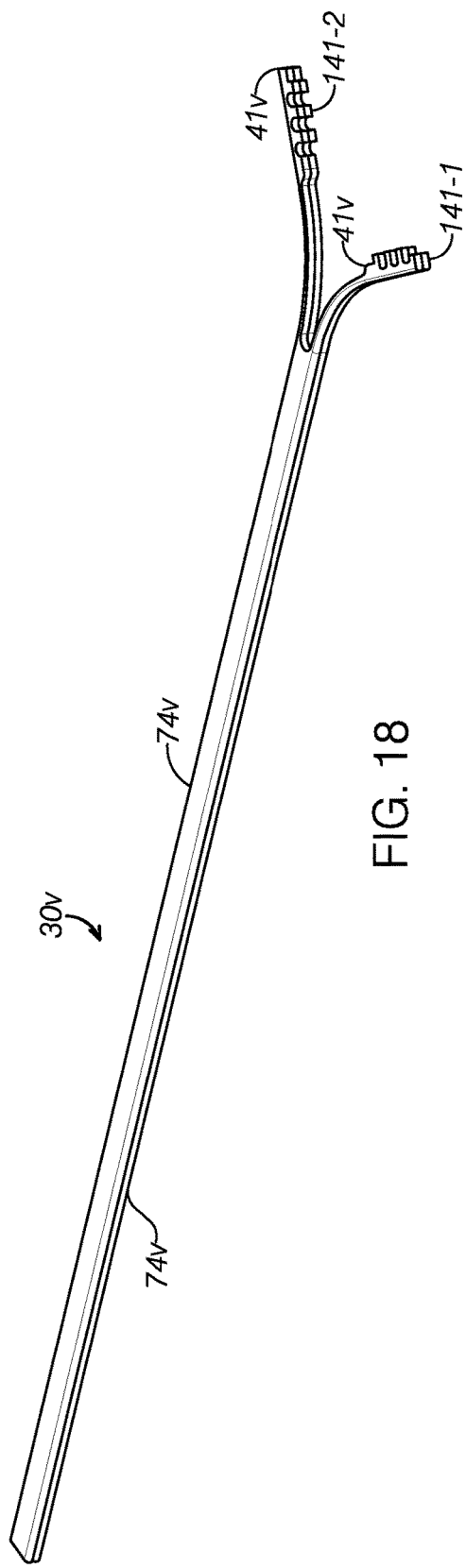
FIG. 18 is a perspective view of an alternative embodiment of a jaw assembly.

FIG. 18 illustrates a dual-stack jaw assembly 30v that inhibits unwanted jaw movement within the hollow shaft by filling up more of space therein with multiple pairs of jaw members 41v stacked on one another. In this preferred embodiment, two pairs of jaw members 41v along with corresponding ribbons 74v are stacked upon each other so as to form a first jaw member stack 141-1 and a second jaw member stack 141-2. The first and second jaw member stacks 141-1, 141-2 diverge from each other in the same manner as unstacked first and second jaw members do as described in the foregoing embodiments. The stacked jaw members in each jaw member stack 141-1, 141-2 preferably move in unison.

The dual-stack jaw assembly 30v may comprise two pairs of jaw members that are either discrete from each other or integral to each other. If discrete pairs of jaw members are stacked, each pair may be connected, adhered, fused or otherwise coupled to the other pair to form a stack. Alternatively, a dual-stack jaw assembly 30v may comprise the equivalent of a discretely stacked pair of jaws by having a single unitary pair of jaws with a greater thickness in the preferred range of 0.4 mm to 4.0 mm. In the preferred embodiment, this inner diameter of the shaft may have a range of 0.75 mm to 2 mm. In the preferred embodiment, the jaw assembly has a thickness that reduces the gap between the exterior of the jaw assembly and the internal surface of the shaft, which distance is preferably between 0.2 mm to 1 mm. This stacked jaw assembly 30v inhibits jaw movement within the shaft while maintaining the flexibility for the jaw members to move through the curves of a shaft or tube.

According to the invention, a preferred suture passing device may comprise a dual stack of any of the preferred jaw assemblies disclosed herein.

Figure 19:
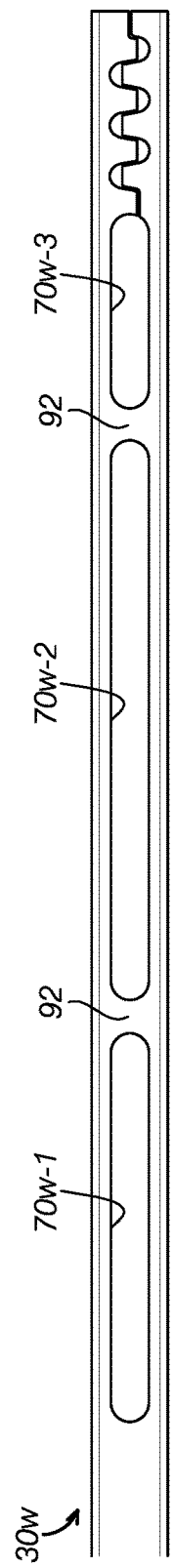
FIG. 19 is a top plan view of an alternative embodiment of a jaw assembly.

FIG. 19 illustrates a jaw assembly 30w having multiple elongate cutouts 70w spaced apart along the jaw assembly axis. In this illustrated embodiment which preferably comprises three cutouts 70w where the length of a particular cutout can be made larger if increased flexibility is required as shown in FIG. 19. One or more bridges 92 can then be added to manipulate the flexibility of the jaw assembly as shown in FIG. 19. The bridges 92 can also be strategically placed to prevent the jaws from crossing within the hollow shaft, which is advantageous in curved tubes (see FIG. 32).

Figure 20:
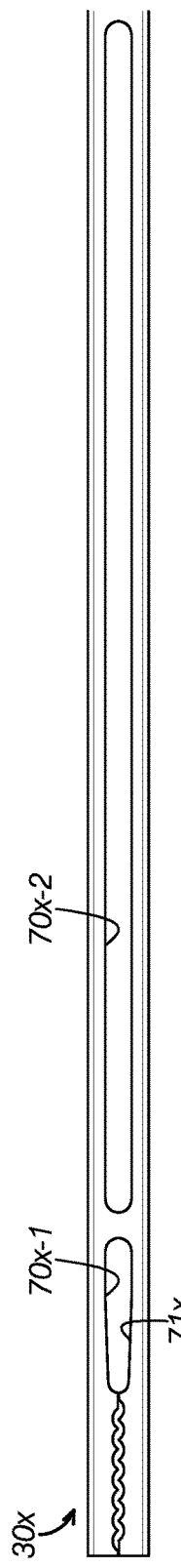
FIG. 20 is a top plan view of an alternative embodiment of a jaw assembly.

FIG. 20 illustrates a jaw assembly 30x having distal elongate cutouts 70x-1 and a proximal elongate cutout 70x-2 with a substantially greater axial length than that of the distal cutout 70x-1. The distal elongate cutouts 70x-1 collectively form a first void 71x directly proximal to the suture capturing mechanism 44x and having a preferred length of 4 mm to 20 mm including the suture capturing mechanism when the jaw assembly 30x is closed. The proximal elongate cutout 70x-2 comprises a second void 70x-2 with a preferred width in the range of 0.03 mm to 0.75 mm and a preferred length in the range of 10 mm to 40 mm.

Figure 21:
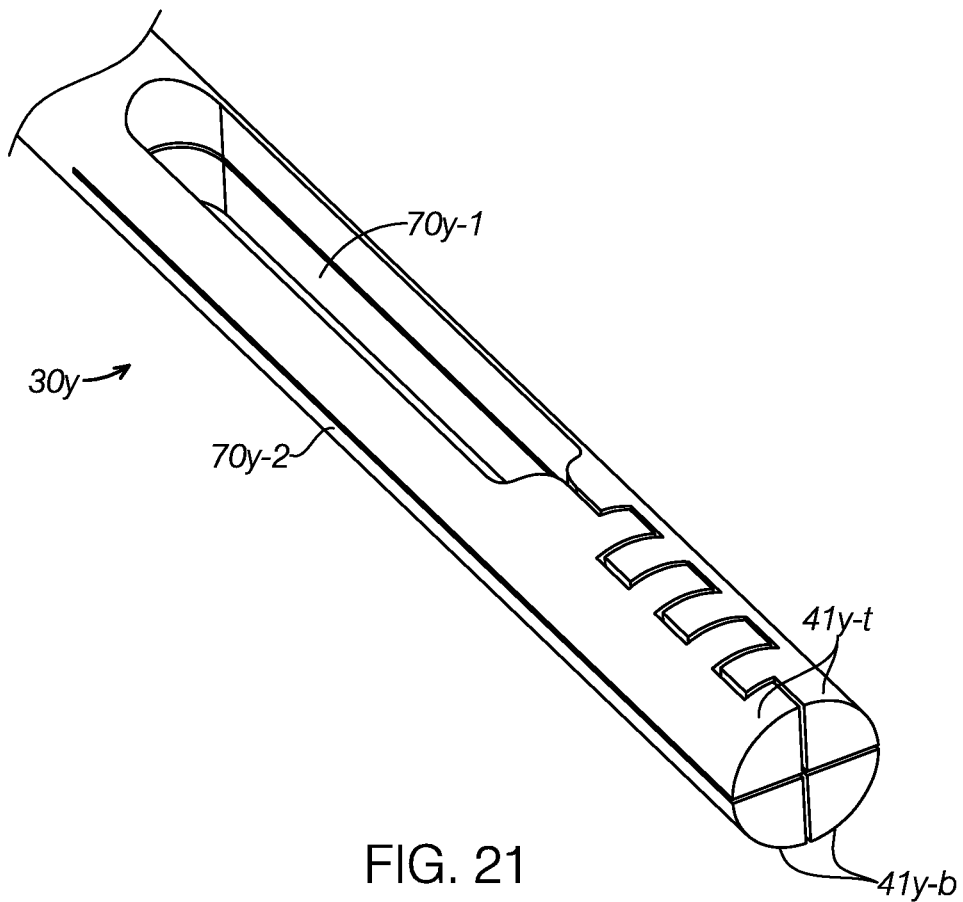
FIG. 21 is a perspective view of an alternative embodiment of a jaw assembly.

FIG. 21 illustrates a cylindrical jaw assembly 30y having four jaw members 41y that collectively form a cylinder. In particular, the jaw assembly 30y comprises a pair of top jaw members 41y-t and a pair of bottom jaw members 41y-b. With some of these thicker cross-sections such as the circle, the stiffness may become too great for bending around corners so it may be advantageous to make cuts 70y-1 along a first plane and additional cuts 70y-2 along a second plane orthogonal to the first plane as shown in FIG. 21.

Figure 22:
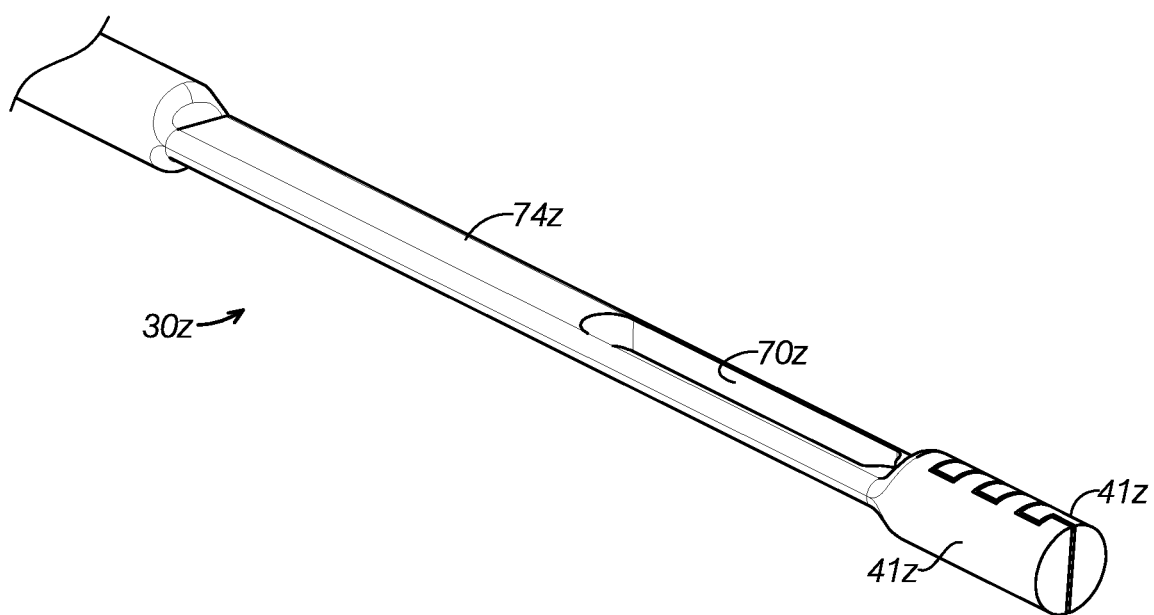
FIG. 22 is a perspective view of an alternative embodiment of a jaw assembly.

FIG. 22 illustrates a jaw assembly 30z having a pair jaw members 41z that collectively form a cylinder. The jaw assembly 30z comprises a planar ribbon 74z with a cutout 70z proximal to the pair of jaws 41z. FIG. 22 shows cuts made to removal material in the flexible section but leaving the round distal portion full to form a cylinder at the distal end of the jaw assembly 30z. In both cases the extra cut is shown 90° to the original cut but it/they can be at any angle that leaves sufficient material for the jaws' operation.

Figure 23:
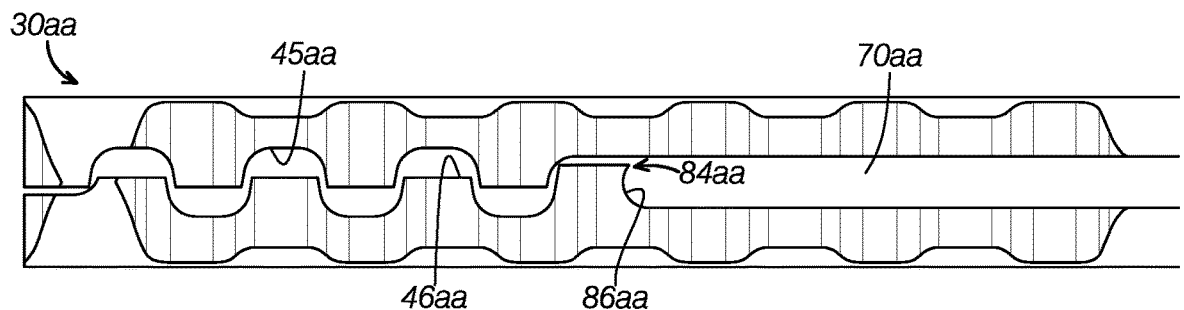
FIG. 23 is a top plan view of an alternative embodiment of a jaw assembly.

FIG. 23 illustrates a jaw assembly 30aa that may be manufactured from a rod as opposed to the ribbon associated with the foregoing embodiments. The jaw assembly 30aa comprises curved valleys 45aa and teeth 46aa. A cutout 70aa defines a hook 86aa located distal to a kerf access 84aa.

Figure 24:
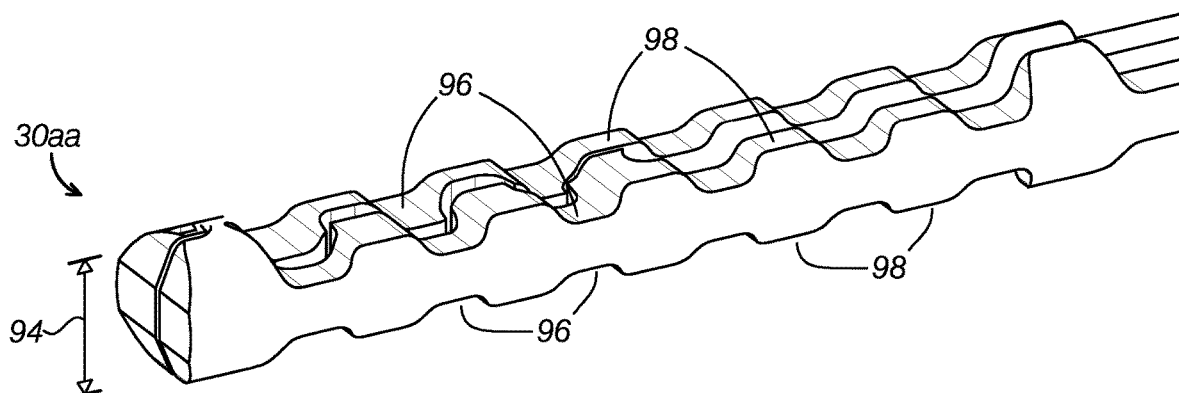
FIG. 24 is a perspective view of an alternative embodiment of a jaw assembly.

In FIG. 24, it will be appreciated that forming the jaw assembly 30aa manufactured from a rod provides a more substantial three-dimensional jaw body than the planar jaw assemblies of foregoing embodiments. This provides the jaw assembly 30aa with a jaw height or thickness 94 such that top indentations and bottom indentations 96, or grooves, may be formed in an alternating pattern with peaks 98. In this preferred embodiment, the top and bottom indentations 98 of a first jaw member 41aa are aligned with those 96 on the second jaw member 41aa.

Figure 25:
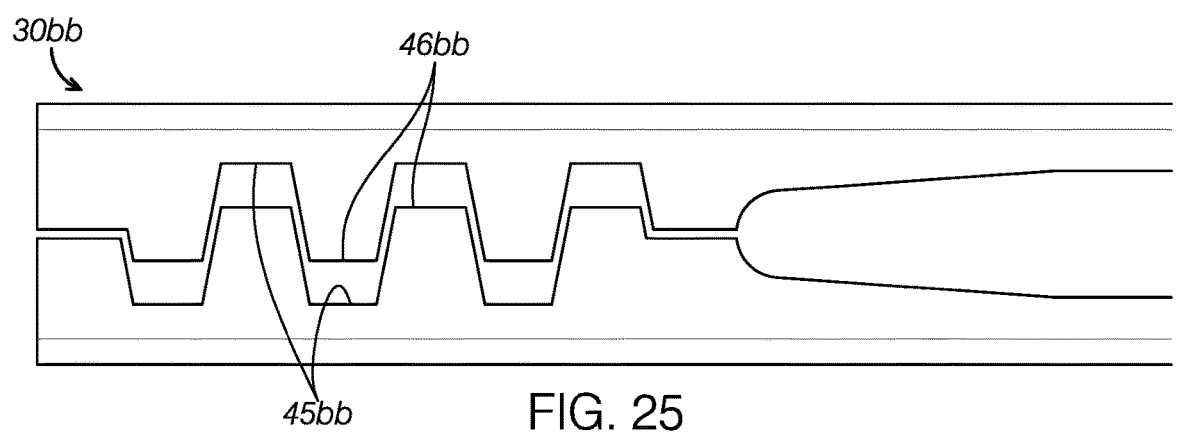
FIG. 25 is a top plan view of an alternative embodiment of a jaw assembly.

FIG. 25 illustrates a jaw assembly 30bb manufactured from a rod having tapered teeth 46bb and tapered valleys 45bb shaped to receive the teeth 46bb to form a nesting relationship.

Figure 26:
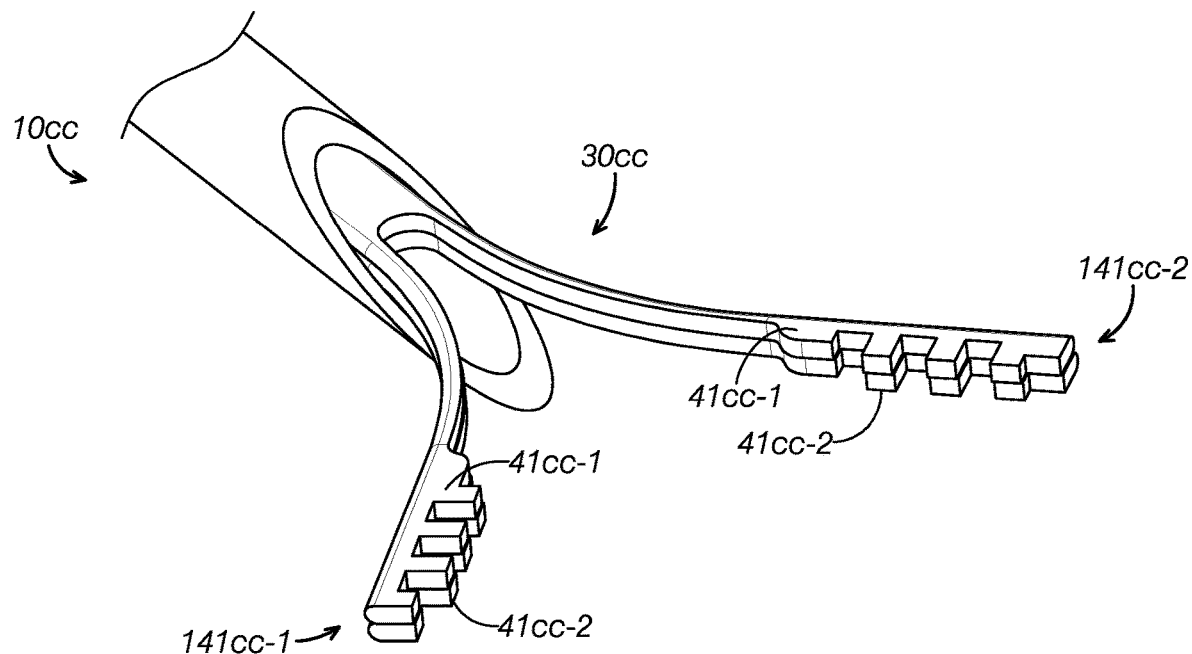
FIG. 26 is a perspective view of a second preferred embodiment of a suture passing device.

In FIG. 26, a second preferred embodiment of a suture passing device 10cc comprises a dual-stack jaw assembly 30cc having two pairs of jaws 41cc-1, 41cc-2 stacked on top of each other. In this preferred embodiment, a first pair of jaws 41cc-1 is stacked on top of a second pair of jaws 41cc-2 to form a first jaw member stack 141cc-1 that diverges away from a second jaw member stack 141cc-2 in the open configuration. The second pair of jaws 41cc-2 can be a replica of the first pair of jaws 41cc-1.

Figure 27:
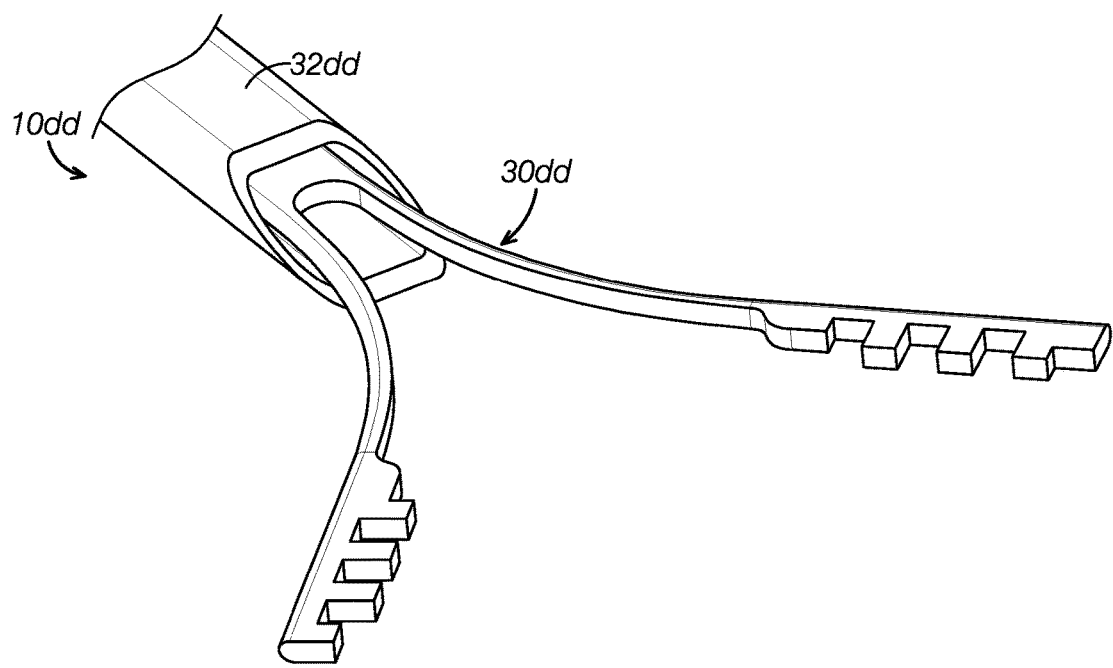
FIG. 27 is a perspective view of a third preferred embodiment of a suture passing device.

FIG. 27 shows a third preferred embodiment of a suture passing device 10dd having a flattened or planar hollow shaft 32dd to minimize unwanted jaw movement within when housing a planar jaw assembly 30dd with a planar jaw ribbon. It will be appreciated that the cross-sectional ribbon profiles shown in FIGS. 10A-10D may also aid in taking up open space within the tube and minimize unwanted movement of the jaws.

Figure 28:
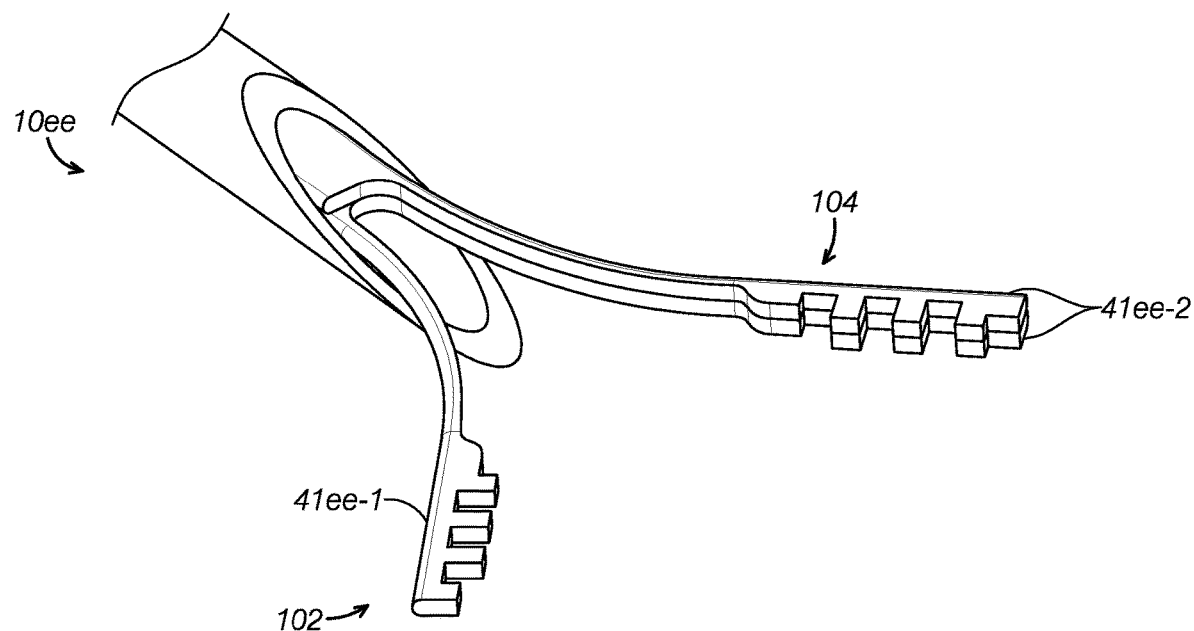
FIG. 28 is a perspective view of a fourth preferred embodiment of a suture passing device.

FIG. 28 shows a fourth preferred embodiment of a suture passing device 10*ee* having a jaw assembly 30*ee* where a first side portion 102 comprises a single jaw member 41*ee*-1 and a second side portion 104 comprises a pair of stacked jaw members 41*ee*-2. It will be appreciated that a jaw assembly 30*ee* may comprise different and asymmetrical jaw members.

Figure 29:
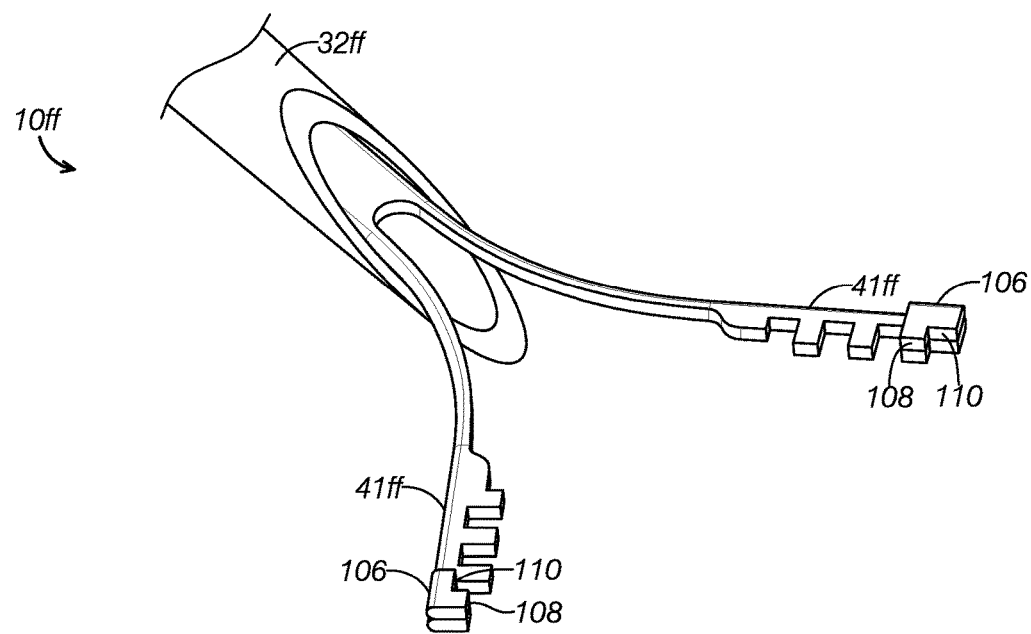
FIG. 29 is a perspective view of a fifth preferred embodiment of a suture passing device.

FIG. 29 illustrates a fifth preferred embodiment of a suture passing device 10*ff* where each jaw member 41*ff* comprises a distal spacer 106 that prevents unwanted jaw movement within the shaft 32*ff*. Each jaw member 41*ff* thus comprises dual distal tips stacked on each other. In a preferred embodiment, the spacers 106 may comprise teeth 108 and valleys 110. Though the spacers are attached to the distal tip in this illustrated embodiment, they can be attached anywhere along the length of the jaw assembly 30*ff* to manipulate the movement within the shaft 32*ff*. Though it is not required that the stacked jaw assemblies be attached the resultant stiffness can be manipulated by strategically attaching the assemblies at various points along the length of the assembly. For example, attaching the assemblies at distal tips as shown in FIG. 29 and leaving the rest of the construct free would result in a jaw assembly with a stiffer tip. This design methodology can also be advantageous to keep the distal tips pieces from crossing within the tube but allowing the shaft portion of the pieces to move relative to each other and thus be more flexible. The opposite can also be done by welding a portion of the shaft but not the jaw tips such that the shafts will move together but the tips can move relative to each other for more flexibility.

The advantage described in the above paragraph is most evident in curved tubes (see FIG. 32) where relative position is important as is flexibility. Though the preferred means of attachment is laser welding there are a variety of methods that can be used to attach the jaw assemblies such as a variety of adhesives.

Figure 30:
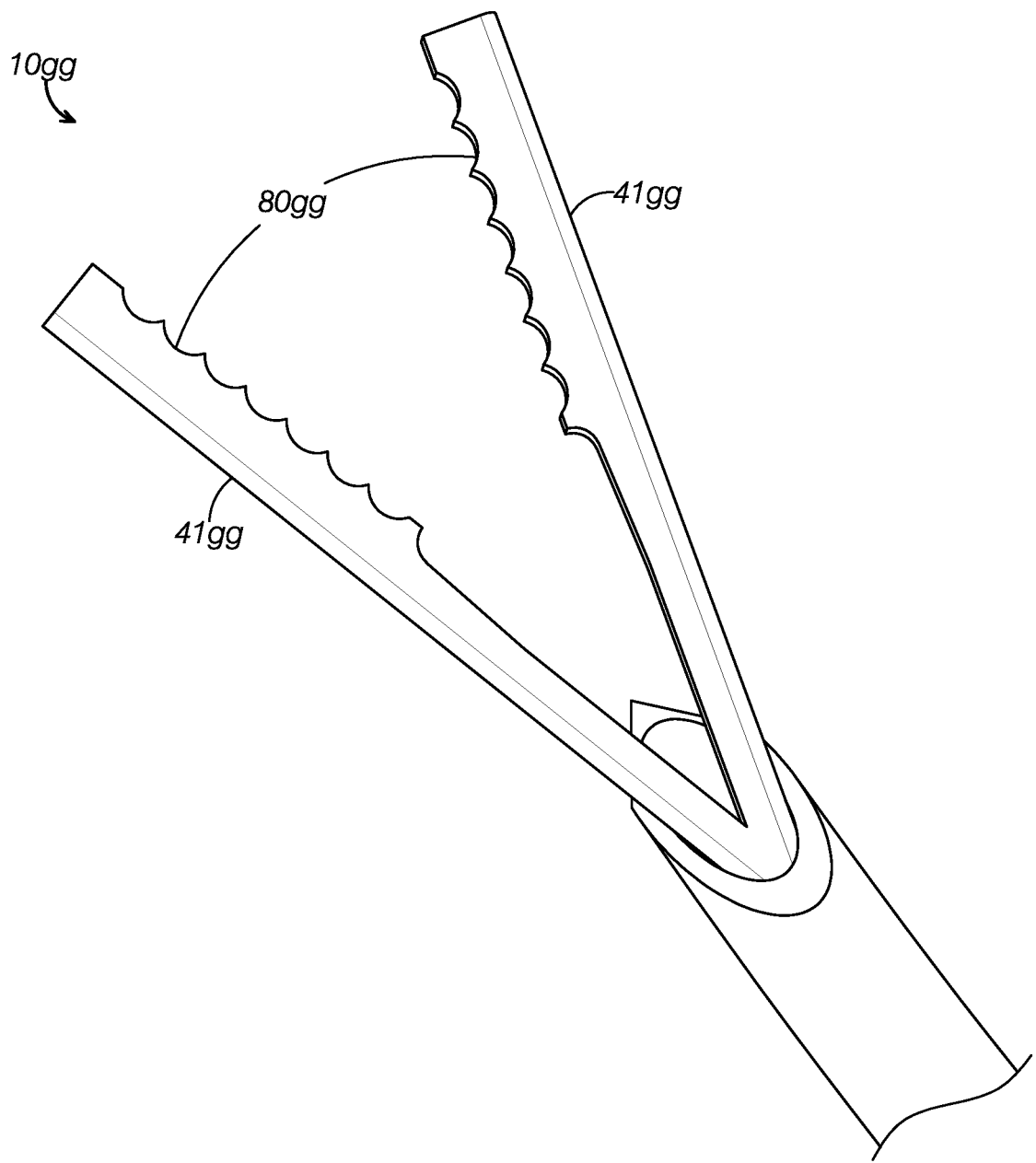
FIG. 30 is a perspective view of a sixth preferred embodiment of a suture passing device.

FIG. 30 illustrates a sixth preferred embodiment of a suture passing device 10*gg* where each jaw member 41*gg* diverges linearly away from each along the distal direction, as opposed to foregoing embodiments where each jaw member increasingly diverges away from each along the distal direction. Each jaw member 41*gg* preferably comprises a scalloped edge 80*gg*.

Figure 31:
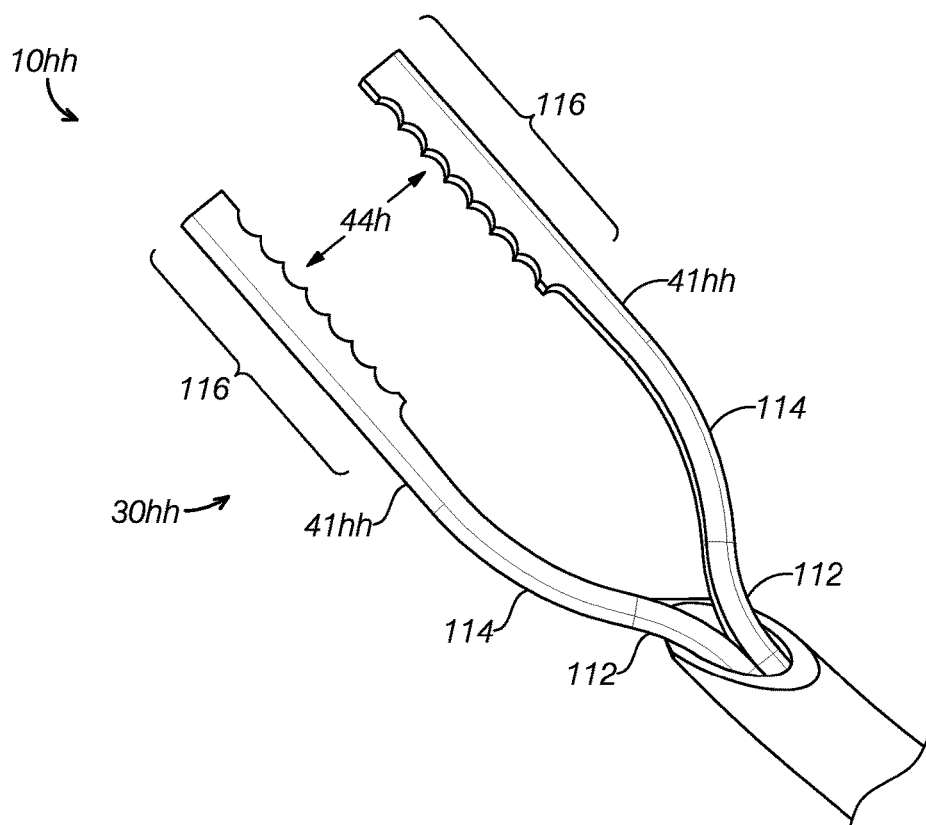
FIG. 31 is a perspective view of an alternative embodiment of a distal needle tip having a curve.

FIG. 31 illustrates a seventh preferred embodiment of a suture passing device 10*hh* having a jaw assembly 30*hh* where each jaw 41*hh* comprises a first proximal bend 112 and a second distal bend 114. The first bend 112 of each jaw 41*hh* is diverging while the second bend 114 of each jaw 41*hh* is converging such that distal jaw portions 116 containing the suture capturing mechanism 44*hh* extend in a substantially parallel manner when the jaw assembly 30*hh* is in the open configuration as shown in FIG. 31.

Figure 32:
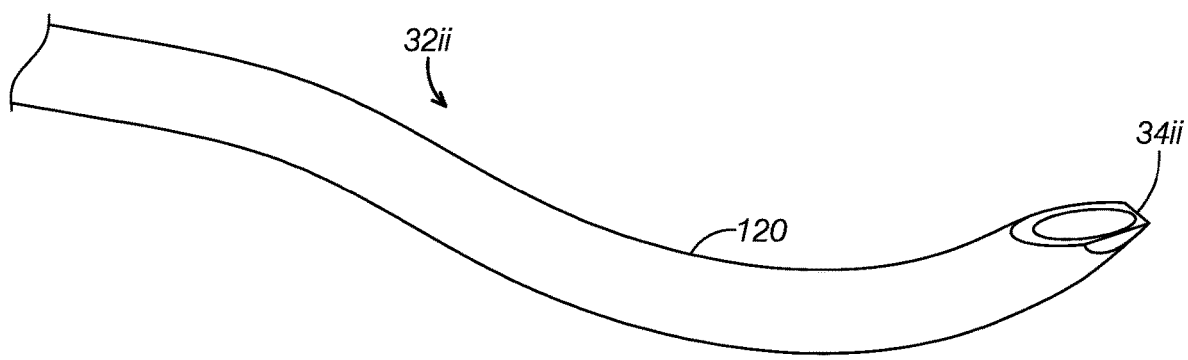
FIG. 32 is a perspective view of a seventh embodiment of a suture passing device.

FIG. 32 illustrates a curved hollow needle shaft 32*ii* that may be used with any of the foregoing preferred embodiments of the suture passing needle. The curved shaft 32*ii* comprises a shaft bend 120 proximal to the sharp needle tip 34*ii*.

In all of the foregoing embodiments where the jaw assembly comprises a proximal ribbon portion, the ribbon may have a thickness in the preferred range of 0.2 mm to 2 mm, and a width in the preferred range of 1 mm to 2 mm.

In all of the foregoing embodiments where the jaw assembly comprises one or more cutouts, the cutout may have a length in the preferred range of 10 mm to 30 mm, and a width in the preferred range of 0.03 mm to 0.75 mm.

In all of the foregoing embodiments where a preferred jaw assembly is shown in the closed configuration but without an accompanying shaft, it is to be expressly understood that the jaw members are shown closed for illustrative purposes only and that such Figures do not imply that the jaw assembly defaults to a closed configuration without a shaft.

It is to be expressly understood that a preferred suturing passing device according to the invention may comprise a dual stack of any foregoing preferred jaw assemblies having any of the foregoing preferred suture capturing mechanisms and any of the foregoing preferred cutouts.

Figure 33:
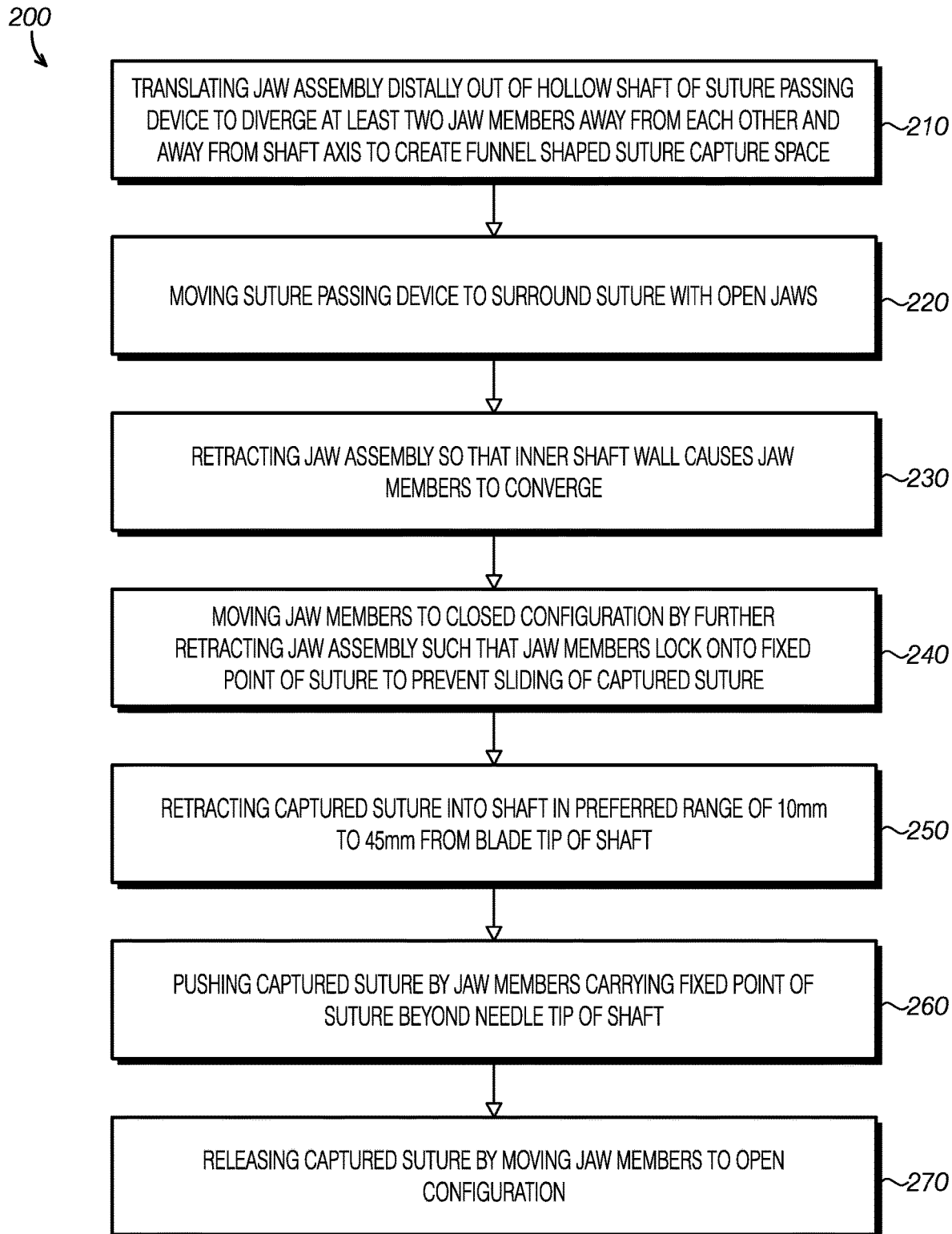
FIG. 33 is a diagram of a preferred method of passing suture.

A preferred method of passing suture 200 is also provided and illustrated in FIG. 33. The method 200 comprises the step 210 of diverging a pair of jaw members of a suture passing device from each other by translating a jaw assembly distally with respect to a hollow shaft to cause the outwardly biased jaw members to exit a distal needle tip. This step 210 creates a preferably flared-out capture space for receiving a portion of suture. This steps 210 also comprises diverging each of the jaw members away from an axis defined by the shaft.

In step 220, the suture passing device is moved to surround a suture with the open jaw members. In step 220, the suture would be disposed within a suture capture space that is defined between the two diverging jaw members and preferably shaped as a funnel.

In step 230, the jaw assembly is retracted with respect to the tube such that the inner wall of the tube causes the jaw members to converge toward each other.

In step 240, the jaw members are moved to a closed configuration so as to capture the suture and lock onto a fixed point of the suture to prevent sliding of the captured suture.

In step 250, the captured suture is retracted into the tube in a preferred range of 10 mm to 45 mm from a blade tip of the shaft.

In step 260, the captured suture is pushed out of the shaft by the jaw members carrying a fixed point of suture to exit the shaft.

In step 270, the suture is released when the jaw members are moved to an open configuration. In the preferred method, the suture is not immediately released as soon as a distal portion of the jaw members exits the shaft. Instead, the suture is preferably retained for a short distance of after the suture capturing mechanism exits the lumen of the shaft.

Figure 34:
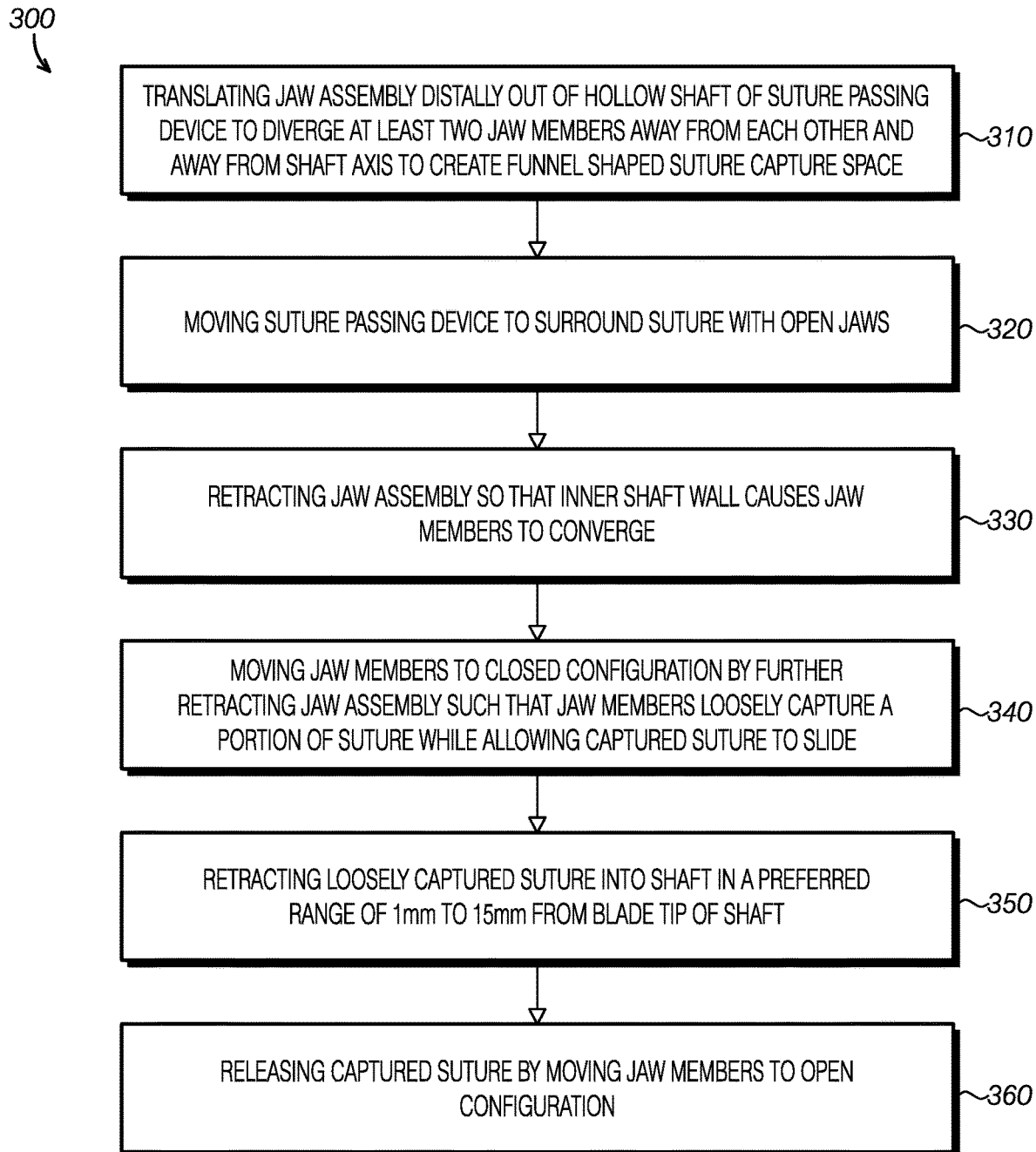
FIG. 34 is a diagram of a further preferred method of passing suture.

A preferred method of passing loosely captured suture 300 is also provided and illustrated in FIG. 34. The method 300 comprises the step 310 of diverging a pair of jaw members of a suture passing device from each other by translating a jaw assembly distally with respect to a hollow shaft to cause the outwardly biased jaw members to exit a distal needle tip. This step 310 creates a preferably flared-out capture space for receiving a portion of suture. This steps 310 also comprises diverging each of the jaw members away from an axis defined by the shaft.

In step 320, the suture passing device is moved to surround a suture with the open jaw members. In step 320, the suture would be disposed within a suture capture space that is defined between the two diverging jaw members and preferably shaped as a funnel.

In step 330, the jaw assembly is retracted with respect to the tube such that the inner wall of the tube causes the jaw members to converge toward each other.

In step 340, the jaw members are moved to a closed configuration so as to loosely capture the suture and while allowing the loosely captured suture to slide.

In step 350, the loosely captured suture is retracted into the tube in a preferred range of 1 mm to 15 mm from a blade tip of the shaft.

In step 360, the suture is released when the jaw members are moved to an open configuration. In the preferred method, the suture is not immediately released as soon as a distal portion of the jaw members exits the shaft. Instead, the suture is preferably retained for a short distance of after the suture capturing mechanism exits the lumen of the shaft.

Terms such as "top," "bottom," "front," "rear," "above," "below" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference. Similarly, an item disposed above another item may be located above or below the other item along a vertical, horizontal or diagonal direction; and an item disposed below another item may be located below or above the other item along a vertical, horizontal or diagonal direction. While some features are shown facing away from gravity, it will be understood that features can be rotated or positioned perpendicular to gravity and work to hold, knot, or cut a suture in the same way as shown.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A suture passing device, comprising:
   a handle;
   a shaft coupled to the handle, the shaft having a shaft axis defining a lumen, the shaft comprising a distal tip;
   a jaw assembly housed within the shaft, the jaw assembly comprising a first jaw member and a second jaw member, the first jaw member and the second jaw member being movable with respect to each other between a closed position and an open position, the first jaw member and the second jaw member forming a distal end of the jaw assembly; and
   an actuating mechanism coupled to the jaw assembly and configured to move the jaw assembly between the closed position and the open position, wherein
   the first jaw member and the second jaw member are biased away from each other when the actuating mechanism moves the jaw assembly distally with respect to the shaft such that the first jaw member and the second jaw member each diverge from the shaft axis when exiting the shaft;
   the first jaw member and the second jaw member are moved to the closed position when the actuating mechanism is moved to retract the jaw assembly proximally with respect to the shaft; and
   at least one cutout formed along a longitudinal length of the jaw assembly, proximate the first jaw member and the second jaw member, at least one of the cutouts being completely surrounded by a jaw ribbon, being unopenable, and retaining its shape when the first and second jaw members are moved between the closed position and the open position, wherein
   when a suture is disposed between the first jaw member and the second jaw member, a captured portion of the suture is moved inside the lumen a distance from about 10 mm to at least 45 mm from the distal tip.

2. The device of claim 1, wherein the jaw assembly comprises teeth.

3. The device of claim 1, wherein the jaw assembly comprises:
   a first plurality of pointy teeth included in the first jaw member to form a first scalloped edge; and a second plurality of pointy teeth included in the second jaw member to form a second scalloped edge.

4. The device of claim 3, wherein the first plurality of teeth is nestable with the second plurality of teeth when the jaw assembly is in the closed position.

5. The device of claim 1, wherein the shaft comprises a bent shaft portion.

6. The device of claim 1, wherein the distal tip comprises a blade tip.

7. The device of claim 1, wherein the jaw assembly further comprises:
 a third jaw member stacked on and movable in unison with the first jaw member; and
 a fourth jaw member stacked on and movable in unison with the second jaw member,
 wherein the third jaw member and the fourth jaw member converge and diverge from each other in unison with the first jaw member and the second jaw member.

8. The device of claim 1, wherein the jaw assembly further comprises a second loose suturing capturing mechanism.

9. The device of claim 1, wherein the jaw assembly comprises a thickness in the range of 0.4 mm to 4.0 mm.

10. The device of claim 9, wherein:
 the jaw assembly comprises an exterior and the shaft comprises an interior shaft surface; and
 a gap between the exterior of the jaw assembly and the interior shaft surface is less than 1 mm.

11. A suture passing device, comprising:
 a handle;
 a shaft coupled to the handle, the shaft having a shaft axis defining a lumen, the shaft comprising a distal tip;
 a jaw assembly housed within the shaft, the jaw assembly comprising a first jaw member and a second jaw member, the first jaw member and the second jaw member being movable with respect to each other between a closed position and an open position, the jaw assembly comprising a push-pull suture capturing mechanism, the first jaw member and the second jaw member forming a distal end of the jaw assembly; and
 an actuating mechanism coupled to the jaw assembly and configured to move the jaw assembly between the closed position and the open position, wherein
 the first jaw member and the second jaw member are biased away from each other towards the open position and moved to the open position when the actuating mechanism moves the jaw assembly distally with respect to the shaft such that the first jaw member and the second jaw member each diverge from the shaft axis when exiting the shaft;
 the first jaw member and the second jaw member are moved to the closed position when the actuating mechanism is moved to retract the jaw assembly proximally with respect to the shaft;
 the push-pull suture capturing mechanism comprises a set of teeth formed on the first jaw member and the second jaw member;
 the set of teeth on the first jaw member and the second jaw member includes a kerf forming a space therebetween when the jaw assembly is in the closed position;
 the first jaw member meshes with the second jaw member such that a side portion of one tooth on the first jaw member is longitudinally adjacent a side member of an adjacent tooth on the second jaw member; and
 at least one cutout formed along a longitudinal length of the jaw assembly, proximate the first jaw member and the second jaw member, at least one of the cutouts being completely surrounded by a jaw ribbon, being unopenable, and retaining its shape when the first and second jaw members are moved between the closed position and the open position.

12. The device of claim 11, wherein the shaft comprises a bent shaft portion.

13. The device of claim 11, wherein the jaw assembly further comprises a second loose suturing capturing mechanism.

14. The device of claim 11, wherein the jaw assembly comprises a cutout proximal to the push-pull suture capturing mechanism.

15. The device of claim 11, wherein the jaw assembly further comprises:
 a third jaw member stacked on the first jaw member; and
 a fourth jaw member stacked on the second jaw member,
 wherein the third jaw member and the fourth jaw member converge and diverge from each other in unison with the first jaw member and the second jaw member.

16. A suture passing device, comprising:
 a handle;
 a shaft coupled to the handle, the shaft having a shaft axis defining a lumen, the shaft comprising a distal tip;
 a jaw assembly housed within the shaft, the jaw assembly comprising a first jaw member and a second jaw member, the first jaw member and the second jaw member being movable with respect to each other between a closed position and an open position;
 a first set of teeth at a distal end of the first jaw member;
 a second set of teeth at a distal end of the second jaw member;
 a void, formed proximal to the first set of teeth and the second set of teeth, between the first jaw member and the second jaw member when in the closed position;
 at least one cutout formed along a longitudinal length of a jaw ribbon disposed proximal to the void, the first jaw member and the second jaw member extending from a distal end of the jaw ribbon, at least one of the cutouts being completely surrounded by the jaw ribbon, being unopenable, and retaining its shape when the first and second jaw members are moved between the closed position and the open position; and
 an actuating mechanism coupled to the jaw assembly and configured to move the jaw assembly between the closed position and the open position, wherein
 the first jaw member and the second jaw member are biased away from each other towards the open position and moved to the open position when the actuating mechanism moves the jaw assembly distally with respect to the shaft such that the first jaw member and the second jaw member each diverge from the shaft axis when exiting the shaft; and
 the first jaw member and the second jaw member are moved to the closed position when the actuating mechanism is moved to retract the jaw assembly proximally with respect to the shaft.

17. The device of claim 16, wherein the first set of teeth and the second set of teeth mesh together in the closed position.

18. The device of claim 16, when a suture is disposed between the first jaw member and the second jaw member, a captured portion of the suture is moved inside the lumen a distance from about 10 mm to at least 45 mm from the distal tip.

* * * * *